(12) United States Patent
Sepassi et al.

(10) Patent No.: US 9,273,034 B2
(45) Date of Patent: Mar. 1, 2016

(54) MEGLUMINE SALT FORMULATIONS OF 1-(5,6-DICHLORO-1H-BENZO[D]IMIDAZOL-2-YL)-1H-PYRAZOLE-4-CARBOXYLIC ACID

(71) Applicant: Janssen Pharmaceutica NV, Beerse (BE)

(72) Inventors: Kia Sepassi, San Diego, CA (US); Michele C. Rizzolio, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/353,241

(22) PCT Filed: Oct. 25, 2012

(86) PCT No.: PCT/US2012/061847
§ 371 (c)(1),
(2) Date: Apr. 21, 2014

(87) PCT Pub. No.: WO2013/063221
PCT Pub. Date: May 2, 2013

(65) Prior Publication Data
US 2014/0329873 A1    Nov. 6, 2014

Related U.S. Application Data

(60) Provisional application No. 61/551,395, filed on Oct. 25, 2011.

(51) Int. Cl.
*C07D 403/04* (2006.01)
*A61K 31/4184* (2006.01)

(52) U.S. Cl.
CPC .......... *C07D 403/04* (2013.01); *A61K 31/4184* (2013.01)

(58) Field of Classification Search
USPC ....................................................... 548/306.1
See application file for complete search history.

(56) References Cited

U.S. PATENT DOCUMENTS

| | | | |
|---|---|---|---|
| 6,093,730 A | 7/2000 | Weidmann | |
| 8,759,345 B2 * | 6/2014 | Hocutt et al. ............ | 514/234.5 |
| 2006/0199836 A1 | 9/2006 | Turtle | |
| 2006/0276477 A1 | 12/2006 | Klaus | |
| 2007/0299086 A1 | 12/2007 | Kawamoto | |
| 2008/0171756 A1 | 7/2008 | Shaw | |
| 2009/0239876 A1 | 9/2009 | Clements | |

FOREIGN PATENT DOCUMENTS

| | | |
|---|---|---|
| DE | 3824658 A1 | 7/1988 |
| DE | 19746287 A1 | 4/1999 |
| DE | 102007048447 A1 | 4/2009 |
| DE | 102007049157 A1 | 4/2009 |
| EP | 0266940 A2 | 5/1988 |
| JP | 2002 504546 A | 2/2002 |
| JP | 2009510152 A | 3/2009 |
| WO | WO 92 22313 A1 | 12/1992 |
| WO | WO 96 39384 A1 | 12/1996 |
| WO | WO 98 39343 A1 | 9/1998 |
| WO | WO 99 43663 A1 | 9/1999 |
| WO | WO 01/42238 A1 | 6/2001 |
| WO | WO 2004 052284 A2 | 6/2004 |
| WO | WO 2004 052285 A2 | 6/2004 |
| WO | WO 2004 108681 A1 | 12/2004 |
| WO | WO 2005 012296 A1 | 2/2005 |
| WO | WO 2005 012297 A1 | 2/2005 |
| WO | WO 2005 063738 A1 | 7/2005 |
| WO | WO 2007 038571 A2 | 4/2007 |
| WO | WO 2007 039297 A1 | 4/2007 |
| WO | WO 2007 070359 A2 | 6/2007 |
| WO | WO 2007 090068 A2 | 8/2007 |
| WO | WO 2007 103905 A2 | 9/2007 |
| WO | WO 2007 136990 A2 | 11/2007 |
| WO | WO 2007 150011 A2 | 12/2007 |
| WO | WO 2008 067871 A1 | 6/2008 |
| WO | WO 2008 082487 A1 | 7/2008 |
| WO | WO 2008 089052 A2 | 7/2008 |
| WO | WO 2008 033739 A2 | 9/2008 |
| WO | WO 2008 130527 A1 | 10/2008 |
| WO | WO 2008 130600 A2 | 10/2008 |
| WO | WO 2008 137060 A1 | 11/2008 |

(Continued)

OTHER PUBLICATIONS

Bastin et al., Organic Process Research & Development, 2000, 4, pp. 427-435.*
Gould, International Journal of Pharmaceutics, 33 (1986), pp. 201-217.*
Stahl et al., Handbook of Pharmaceutical Salts, Properties, Selection, and Use, (Wiley-VCH, 2008), pp. 265-327.*
K. Sepassi, et al., poster, "Multi-factorial approach to the development of a topical formulation of a new molecular entity", American Association of Pharmaceutical Scientists Meeting, Oct. 25, 2011.*
Abbott et al., "Stromal Cell-Derived Factor-1[alpha] Plays a Critical Role in Stem Cell Recruitment to the Heart After Myocardial Infarction but Is Not Sufficient to Induce Homing in the Absence of Injury" 2004, *Circulation*, 110(21), pp. 3300-3305.

(Continued)

*Primary Examiner* — Laura L. Stockton

(57) ABSTRACT

The meglumine salt of 1-(5,6-dichloro-1H-benzo[d]imidazol-2-yl)-1H-pyrazole-4-carboxylic acid (compound (1)) and pharmaceutically acceptable formulations thereof are described. Such compounds may be used in pharmaceutical compositions and methods for the treatment of disease states, disorders, and conditions mediated by prolyl hydroxylase activity.

compound (1)

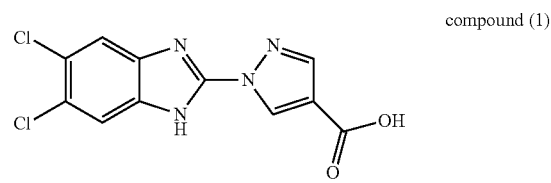

3 Claims, 8 Drawing Sheets

(56) References Cited

FOREIGN PATENT DOCUMENTS

| WO | WO 2008 137084 A2 | 11/2008 |
|---|---|---|
| WO | WO 2009 073669 A1 | 6/2009 |
| WO | WO 2009 086044 A1 | 7/2009 |
| WO | WO 2009 086592 A1 | 7/2009 |
| WO | WO 2009 089547 A1 | 7/2009 |
| WO | WO 2009 108496 A1 | 9/2009 |
| WO | WO 2009 108497 A1 | 9/2009 |
| WO | WO 2009 108499 A1 | 9/2009 |
| WO | WO 2009 117269 A1 | 9/2009 |
| WO | WO-2009/134750 A1 * | 11/2009 |

OTHER PUBLICATIONS

Al-Sheikh et al., "Disturbance in the HIF-1 alpha pathway associated with erythrocytosis: Further evidences brought by frameshift and nonsense mutations in the prolyl hydroxylase domain protein 2 (PHD2) gene" 2008, *Blood Cells Mol Dis.*, 40, pp. 160-165.

Aquilina et al. "Polypeptidwe Modification and Cross Linking by Oxidized 3-Hydroxylynurenine" Biochemistry 2000 vol. 39 pp. 16176-16184.

Aragones et al., "Deficiency or inhibition of oxygen sensor Phd1 induces hypoxia tolerance by reprogramming basal metabolism" 2008, *Nature Genetics*, 40(2), pp. 170-180.

Arcasoy, "The non-haematopoietic biological effects of erythropoietin", *British Journal of Haematology*, 2008, 141 (1), pp. 14-31.

Armellini et al."The effects of high altitude trekking on body composition and resting metabolic rate", *Hormone & Metabolic Research*, 1997, 29(9), pp. 458-461.

Bagshawe et al. "Antibody-Directed Enzyme Prodrug Therapy: A Review" *Drug Dev Res*, 1995, 34, pp. 220-230.

Barrett et al ."Pharmacological Characterization of 1-(5-chloro-6-(trifluoromethoxy)-1Hbenzoimidazol-2-yl)-1H-pyrazole-4-carboxylic acid (JNJ-42041935), a Potent and SelectiveHypoxia-Inducible Factor Prolyl Hydroxylase Inhibitor" Mol. Pharmacol. 2011 vol. 79(6)pp. 910-920.

Berge, et al., "Pharmaceutical Salts", *J Pharm Sci.*, 1977, 66, pp. 1-19.

Bernaudin et al., "Normobaric hypoxia induces tolerance to focal permanent cerebral ischemia in association with an increased expression of hypoxia-inducible factor-1 and its target genes, erythropoietin and VEGF, in the adult mouse brain" 2002, *J Cereb Blood Flow Metab.*, 22(4), pp. 393-403.

Bernhardt et al., "Organ protection by hypoxia and hypoxia-inducible factors" 2007, *Methods Enzymol.*, 435, pp. 221-245.

Berra et al., "HIF prolyl-hydroxylase 2 is the key oxygen sensor setting low steady-state levels of HIF-1alpha in normoxia" 2003, *EMBO (European Molecular Biology Organization) Journal*, 22(16), pp. 4082-4090.

Bertolini et al. "A New Rational Hypothesis for the Pharmacophore of the Active Metabolite of Leflunomide, A Potent Immunosuppressive Drug" *J. Med. Chem.*, 1997, 40, pp. 2011-2016.

Bodor et al.,"Novel Approaches to the Design of Safer Drugs: Soft Drugs and Site-Specific Chemical Delivery Systems" *Adv Drug Res.* 1984, 13, 255-331.

Braliou et al., "2-Oxoglutarate-dependent oxygenases control hepcidin gene expression" 2008, *Journal of Hepatology*, 48 (5), pp. 801-810.

Breen, "VEGF in biological control" 2007, *J Cell Biochem.*, 102(6), pp. 1358-1367.

Bundgaard, Design of Prodrugs (Elsevier Press, 1985), Table of Contents Only.

Cai et al., "Complete loss of ischaemic preconditioning-induced cardioprotection in mice with partial deficiency of HIF-1 alpha" 2008, *Cardiovasc Res.*, 77(3), pp. 463-470.

Carmeliet,"Manipulating angiogenesis in medicine" 2004, *J Intern Med.*, 255(5), pp. 538-561.

Carrière et al. "Mitochondrial Reactive Oxygen Species Control the Transcription Factor CHOP-10/GADD153 and Adipocyte Differentiation: A Mechanism for Hypoxia-Dependent Effect" 2004, *J Biol Chem.*, 279(39), pp. 40462-40469.

Chang et al "Age Decreases Endothelial Progenitor Cell Recruitment Through Decreases in Hypoxia-Inducible Factor 1⊕ Stabilization During Ischemia" Circulation 2007 vol. 116 pp. 2818-2829.

Ceradini et al., "Homing to hypoxia: HIF-1 as a mediator of progenitor cell recruitment to injured tissue" 2005, *Trends Cardiovasc Med.*, 15(2), pp. 57-63.

Ceradini et al., "Progenitor cell trafficking is regulated by hypoxic gradients through HIF-1 induction of SDF-1" 2004, *Nat Med.*, 10(8), pp. 858-864.

Chin et al. "Hypoxia-inducible factor 1alpha stabilization by carbon monoxide results in cytoprotective preconditioning" 2007, *Proc Natl Acad Sci. U.S.A.*, 104(12), pp. 5109-5114.

Collins-Cafiero "O-Nitroaniline Derivatives. Part 14. 1,2 Cyclisations Leading to Benzimidazole N-Oxides, N-Hydroxybenzimidazolones and N-Hydroxyquinoxaline-2,3-Diones: A Mechanistic Bordeline" Journal of the Chemical Society Perkin Transactions—1 Organic and Bio Organic Chemistry 1997 vol. 9 pp. 1375-1384.

Darling et al., "'Postconditioning' the human heart: Multiple balloon inflations during primary angioplasty may confer cardioprotection." 2007, *Basic Res Cardiol.*, 2007, 102(3), pp. 274-278.

Das et al., "Molecular mechanism of preconditioning", *IUBMB Life*, 2008, 60(4), pp. 199-203.

Dubey et al "Mass Spectral Studies of 2,4-Disubstituted Benzimidazoles" Indian Journal of Chemistry 1987 vol. 26b pp. 395-397.

Ebert et al. "Hypoxia and Mitochondrial Inhibitors Regulate Expression of Glucose Transporter-1 via Distinct Cis-acting Sequences" 1995, *J Biol Chem.*, 270(49), pp. 29083-29089.

Elson et al., "Induction of hypervascularity without leakage or inflammation in transgenic mice overexpressing hypoxia-inducible factor-1 alpha" 2001, *Genes Dev.*, 15(19), pp. 2520-2532.

Epstein et al., "*C. elegans* EGL-9 and mammalian homologs define a family of dioxygenases that regulate HIF by prolyl hydroxylation" 2001, *Cell*, 107(1), pp. 43-54.

Feldser et al., "Reciprocal positive regulation of hypoxia-inducible factor 1alpha and insulin-like growth factor 2", *Cancer Res.* 1999 59 (16), pp. 3915-3918.

Firth et al. "Oxygen-regulated control elements in the phosphoglycerate kinase 1 and lactate dehydrogenase A genes: Similarities with the erythropoietin 3' enhancer" 1994, *Proc Natl Acad Sci. USA*, 91(14), pp. 6496-6500.

Fleisher et al. "Improved Oral Delivery: Solubility Limitations Overcome by the Use of Prodrugs" Advanced Drug Delivery Review, 1996, 19, pp. 115-130.

Floyd et al., "Effects of prolyl hydroxylase inhibitors on adipogenesis and hypoxia inducible factor 1 alpha levels under normoxic conditions" 2007, *J Cell Biochem.*, 101(6), pp. 1545-1557.

Fukuda et al., "HIF-1 regulates cytochrome oxidase subunits to optimize efficiency of respiration in hypoxic cells" 2007, *Cell*,129(1), pp. 111-122.

Garcia-Sosa et al "Including Tightly-Bound Water Molecules in de Novo Drug Design. Exemplification through the Silico Generation of Poly(ADP-ribose)polymerase Ligands" J Chem Inf Model 2005 vol. 45 pp. 624-633.

Greenwald et al. "Drug delivery systems. 2. Camptothecin 20-O-poly(ethylene glycol) ester transport forms" Journal of Medicinal Chemistry, 1996, 39(10), pp. 1938-1940.

Grosfeld et al."Hypoxia-inducible Factor 1 Transactivates the Human Leptin Gene Promoter" 2002, *J Biol Chem.*, 277(45), pp. 42953-42957.

Gustafsson et al., "Exercise-induced angiogenesis-related growth and transcription factors in skeletal muscle, and their modification in muscle pathology." *Frontiers in Bioscience*, 2001, 6, pp. D75-D89.

Hirota, Simon A., et al.; "Targeting hypoxia-inducible factor-1 (HIF-1) signaling in therapeutics; implications for the treatment of inflammatory bowel disease." *Recent patents on inflammation & allergy drug discovery* 3.1 (2009): 1-16.

Hu et al., "Transplantation of hypoxia-preconditioned mesenchymal stem cells improves infarcted heart function via enhanced survival of

(56) References Cited

OTHER PUBLICATIONS implanted cells and angiogenesis", *Journal of Thoracic & Cardiovascular Surgery,* 2008 135(4), pp. 799-808.
Ivan et al. "Biochemical purification and pharmacological inhibition of a mammalian prolyl hydroxylase acting on hypoxia-inducible factor" *Proc Natl Acad Sci. USA,* 2002, 99(21), pp. 13459-13464.
Ivan, Mircea, et al. "HIFα targeted for VHL-mediated destruction by proline hydroxylation: implications for O2 sensing." *Science* 292. 5516 (2001): 464-468.
Jaakkola et al., "Targeting of HIF-[alpha] to the von Hippel-Lindau Ubiquitylation Complex by O2-Regulated Prolyl Hydroxylation" *Science,* 2001, 292(5516), pp. 468-472.
Kaelin, "Proline hydroxylation and gene expression" *Annu Rev Biochem.,* 2005, 74, pp. 115-128.
Kandeel et al., "Synthesis and Chemical Reactivity of Benzimidazol-2-YL Hydrazonyl Chlorides" *Polish Journal of Chemistry* (1983), 57(1-3), 327-31.
Kanelakis et al Characterization of a Robust Enzymatic Assay for Inhibitors of 2-Oxoglutarate-Dependent Hydroxylases. J. Biomol. Screen. 2009 vol. 14(6) pp. 627-635.
Ke et al., "Hypoxia-inducible factor-1 (HIF-1)", *Mol Pharmacol.* 2006, 70(5), pp. 1469-1480.
Kelly et al., "Cell type-specific regulation of angiogenic growth factor gene expression and induction of angiogenesis in nonischemic tissue by a constitutively active form of hypoxia-inducible factor 1", *Circ Res.,* 93(11), 2003, pp. 1074-1081.
Kim et al., "HIF-1-mediated expression of pyruvate dehydrogenase kinase: A metabolic switch required for cellular adaptation to hypoxia, *Cell Metab.,*" 2006 3(3), pp. 177-185.
Kojima I et al.,"Protective role of hypoxia-inducible factor-2 alpha against ischemic damage and oxidative stress in the kidney" *J Am Soc Nephrol.,* 2007, 18 (4), pp. 1218-1226.
Krogsgaard-Larsen et al., Textbook of Drug Design and Development, eds Harwood Academic Publishers 1981, Table of Contents and Index Only.
LeCount et al., "Cyclisation of Heterocyclic Hydrazones Prepared from Dimethyl Acetyl-enedicarboxylate" *Journal of the Chemical Society, Perkin Transactions 1: Organic and Bio-Organic Chemistry* (1972-1999) (1974), (2), pp. 297-301.
Lee et al. "Hypox-inducible Factor-1 Mediates Transcriptional Activation of the Heme Oxygenase-1 Gene in Response to Hypoxia", *J Biol Chem.,* 1997, 272(9), pp. 5375-5381.
Lin et al. "Differentiation Arrest by Hypoxia", *J Biol Chem.,* 2006, 281(31), pp. 30678-30683.
Lipunova et al.,"Benzimidazol[1,2-a]pyrazol-1,5-c]quinazoline: a novel heterocyclic system" *Mendeleev Communications* 1996, 1 pp. 15-17.
Lipunova et al., "Synthesis and Cyclization of Derivatives of 3-Heterylhydrazino-2-polyfluorobenzoylacrylic Acid" *Russian Journal of Organic Chemistry* (Translation of Zhurnal Organicheskoi, Khimii) 1997, 33(10), pp. 1476-1486.
Liu et al., "Hypoxia Regulates Vascular Endothelial Growth Factor Gene Expression in Endothelial Cells: Identification of a 5 prime Enhancer", *Circ Res.,* 1995, 77(3), pp. 638-643.
Ljublinskaya et al "A Mild Conversion of the 2,4-Dinitrophenyl-Glycyl-Moiety to a Derivative of 6-Nitrobenzimidazol-1-Oxide" *Tetrahedron Letters* 1972 vol. 47 pp. 4511-4514.
Lok et al. "Identification of a Hypoxia Response Element in the Transferrin Receptor Gene", *J Biol Chem.,* 1999, 274(34), pp. 24147-24152.
Luttun et al., "Placental growth factor (PIGF) and its receptor Flt-1 (VEGFR-1): Novel therapeutic targets for angiogenic disorders" *Series Information: Annals of the New York Academy of Sciences,* 2002, 979, pp. 80-93.
Mace et al., "Sustained expression of Hif-1 alpha in the diabetic environment promotes angiogenesis and cutaneous wound repair", *Wound Repair Regen.,* 2007, 15(5), pp. 636-645.
Mallick et al., "Ischemia-Reperfusion Injury of the Intestine and Protective Strategies Against Injury", *Digestive Diseases & Sciences,* 2004, 49(9), pp. 1359-1377.

Metzen E. et al., "Intracellular localisation of human HIF-1alpha hydroxylases: Implications for oxygen sensing" *J Cell Sci.,* 2003,116, pp. 1319-1326.
Mukhopadhyay et al. "Role of Hypoxia-inducible Factor-1 in Transcriptional Activation of Ceruloplasmin by Iron Deficiency", *J Biol Chem.,* 2000, 275(28), pp. 21048-21054.
Murry et al. "Preconditioning with ischemia: a delay of lethal cell injury in ischemic myocardium", *Circulation,* 1986 74(5), pp. 1124-1136.
Nagai et al "Becaplermin: Recombinant Platelet Derived Growth Factor, a New Treatment for Healing Diabetic Foot Ulcers" Exp Opin Biol Ther 2002 vol. 2(2) pp. 211-218.
Natarajan et al., "Hypoxia inducible factor-1 upregulates adiponectin in diabetic mouse hearts and attenuates post-ischemic injury" 2008, J Cardiovasc Pharmacol., 51(2), pp. 178-187.
Natarajan et al., "Hypoxia inducible factor-1 activation by prolyl 4-hydroxylase-2 gene silencing attenuates myocardial ischemia reperfusion injury", *Circulation Res.,*2006, 98(1), pp. 133-140.
Nishiguchi, K. et al.,. "Sulfonyl Chloride Formatin from Thiol Derivatives by N-Chlorosuccinimide Mediated Oxidation" *Synthesis,* 2006, 24, pp. 4131-4134.
Pajusola et al., "Stabilized HIF-1alpha is superior to VEGF for angiogenesis in skeletal muscle via adeno-associated virus gene transfer" *FASEB Journal,* 2005, 19(10), pp. 1365-1367.
Papandreou et al., "HIF-1 mediates adaptation to hypoxia by actively downregulating mitochondrial oxygen consumption" *Cell Metab.,* 2006, 3(3), pp. 187-197.
Pasupathy et al., "Ischaemic preconditioning protects against ischaemia/reperfusion injury: emerging concepts". *European Journal of Vascular and Endovascular Surgery,* 2005, 29, pp. 106-115.
Paulekuhn, et al., "Trends in Active Pharmaceutical Ingredient Salt Selection based on Analysis of the Orange Book Database", *J. Med. Chem.,* 2007, 50:6665-72.
Percy et al. "A family with erythrocytosis establishes a role for prolyl hydroxylase domain protein 2 in oxygen homeostasis" *PNAS,* 2006, 103(3), pp. 654-659.
Peyssonnaux et al., "Critical role of HIF-1 alpha in keratinocyte defense against bacterial infection" *J Invest Dermatol.,* 2008 128(8), pp. 1964-1968.
Peyssonnaux et al., "HIF-1 alpha expression regulates the bactericidal capacity of phagocytes". *J Invest Dermatol.,* 2005, 115(7), pp. 1806-1815.
Peyssonnaux et al., "Regulation of iron homeostasis by the hypoxia-inducible transcription factors (HIFs)." *J Clin Invest.,* 2007, 117(7), pp. 1926-1932.
Pfander et al "HIF-1a Controls Extracellular Matrix Synthesis by Epiphyseal Chondrocytes" J Cell Sci 2003 116(9) pp. 1819-1826.
Povstyanoi et al., "2-hydrazino(alkylhydrazino)benzimidazole, in reaction with 3-aroylpropanon-2-ic acids" Ukrainskii Khimicheskii Zhurnal (Russian Edition) (1990), 56(10), pp. 1089-1092.
Rabinowitz. et al. "Inhibitors of HIF Prolyl Hydroxylases" Annual Reports in Medicinal Chemistry. 2010 vol. 45 Chapter 8 pp. 123-139 Academic Press Elsevier Inc.
Rabinowitz et al "Structure Based Design and Biological Evaluation of Benzimidazole HIF Prolyl Hydroxylase Inhibitors for the Treatment of Anemia" Abstracts of Papers, 239th ACS National Meeting, San Francisco, CA, United States, Mar. 21-25, 2010.
Rabinowitz, M. "Inhibition of Hypoxia-Inducible Factor Prolyl Hydroxylase Domain Oxygen Sensors: Tricking the Body into Mounting Orchestrated Survival and Repair Responses" *J. Med. Chem.,* in press, 2013, pp. 9369-9402.
Rastogi et al "Synthesis of Benzimidazole-2-Carboxamides as Potential Anthelmintic Agents" Indian J. Chem 1979 vol. 18b pp. 464-467.
Robinson et al., "Mucosal protection by hypoxia-inducible factor prolyl hydroxylase inhibition" *Gastroenterology,* 2008, 134(1), pp. 145-155.
Rolfs et al. "Oxygen-regulated transferrin expression is mediated by hypoxia-inducible factor-1" *J Biol Chem.,*1997, 272(32), pp. 20055-20062.
Scheuermann et al., "Hypoxia-inducible factors Per/ARNT/Sim domains: structure and function" *Methods Enzymol.,* 2007, 435, pp. 3-24.

(56) References Cited

OTHER PUBLICATIONS

Schmid et al., "HIF-1 and p53: Communication of Transcription Factors under Hypoxia" Journal of Cellular & Molecular Medicine, 2004, 8(4), pp. 423-431.

Schultz et al., "Hypoxia and hypoxia-inducible factor-1 alpha promote growth factor-induced proliferation of human vascular smooth muscle cells" *Am J Physiol Heart Circ Physiol.*, 2006, 290(6), pp. H2528-H2534.

Semenza et al. "A nuclear factor induced by hypoxia via de novo protein synthesis binds to the human erythropoietin gene enhancer at a site required for transcriptional activation", , *Mol Cell Biol.*, 1992, 12(12), pp. 5447-5454.

Semenza et al., "Vasculogenesis, angiogenesis, and arteriogenesis: Mechanisms of blood vessel formation and remodeling", *J Cell Biochem.*, 102(4), 2007, pp. 840-847.

Semenza, "Hypoxia-inducible factor 1: Oxygen homeostasis and disease pathophysiology" *Trends in Molecular Medicine*, 2001, 7(8), pp. 345-350.

Semenza, "Oxygen-dependent regulation of mitochondrial respiration by hypoxia-inducible factor 1", *Biochem J.*, 405 (1), 2007, pp. 1-9.

Semenza, "Regulation of tissue perfusion in mammals by hypoxia-inducible factor 1." *Exp Physiol.*, 2007, 92(6), pp. 988-991.

Semenza, "Hypoxia-inducible factor 1 (HIF-1) Pathway" *Science's Stke (Signal Transduction Knowledge Environment )*2007, 407(cm8), pp. 1-3.

Senga et al., "Synthesis of Pyrazolo [1',5':1,2]-1,3,5-triazino[5,6-]benzimidazoles" *Journal of Heterocyclic Chemistry* 1975, 12(5):899-901.

Shan et al. "Prodrug strategies based on intramolecular cyclization reactions", *Journal of Pharmaceutical Sciences* 1997, 86(7), pp. 765-767.

Shaw, "Glucose metabolism and cancer" *Curr Opin Cell Biol.*, 2006, 18(6), pp. 598-608.

Shyu et al., "Intramyocardial injection of naked DNA encoding HIF-1alpha/VP16 hybrid to enhance angiogenesis in an acute myocardial infarction model in the rat." *Cardiovasc Res.*, 2002, 54(3), pp. 576-583.

Siddiq et al. "Hypoxia-inducible Factor Prolyl 4-Hydroxylase Inhibition: A Target for Neuroprotection in the Central Nervous System", *J Biol Chem.*, 2005, 280(50), pp. 41732-41743.

Simon et al., "The role of oxygen availability in embryonic development and stem cell function" *Nature Reviews Molecular Cell Biology*, 2008, 9(4), pp. 285-296.

Singh et al., "Reaction of 2-hydrazinobenzimidazole with B-diketones: A Structural Reinvestigation" *Indian Journal of Chemistry, Section B: Organic Chemistry Including Medicinal Chemistry*, 1993, 32B(2):262-5.

Stahl & Wermuth Handbook of Pharmaceutical Salts, Properties, Selection and Use Stahl and Wermuth eds Wiley-VCH and VHCA Zurich 2002, Cover Page Only.

Steed, "Clinical Evaluation of Recombinant Human Platelet-Derived Growth Factor for the Treatment of Lower Extremity Ulcers" 2006, *Plast Reconstr Surg.*, 117(7 Suppl), pp. 143S-149S.

Tacchini et al. "Transferrin Receptor Induction by Hypoxia. HIF-1-Mediated Transcriptional Activation and Cell-Specific Post-Transcriptional Regulation", *J Biol Chem.*, 1999, 274(34), pp. 24142-24146.

Terzioglu et al "Synthesis and Structure Activity Relationships of Indole and Benzimidazole Piperazines as Histamine H4 Receptor Antagonist" Bioorg & Med Chem Letters 2004 vol. 14 pp. 5251-5256.

Thangarajah et al "HIF-a Dysfunction in Diabetes" Cell Cycle 2010 vol. 9 pp. 75-79.

Thangarajah et al "The Molecular Basis for Impaired Hypoxia-Induced VEGF Expression in Diabetic Tissues" PNAS 2009 vol. 106(32) pp. 13505-13510.

Thurston et al., "Angiopoietin-1 protects the adult vasculature against plasma leakage" *Nature Medicine*, 2000, 6(4), pp. 460-463.

Thurston et al., "Leakage-resistant blood vessels in mice transgenically overexpressing angiopoietin-1", *Science*,1999, 286, pp. 2511-2514.

Vincent et al., "Angiogenesis Is Induced in a Rabbit Model of Hindlimb Ischemia by Naked DNA Encoding an HIF-1[alpha]/VP16 Hybrid Transcription Factor", *Circulation*, 2000, 102 (18), pp. 2255-2261.

Wang et al. "Characterization of hypoxia-inducible factor 1 and regulation of DNA binding activity by hypoxia" *J Biol Chem.*, 1993, 268(29), pp. 21513-21518.

Wang et al. "General involvement of hypoxia-inducible factor 1 in transcriptional response to hypoxia" *Proceedings of the National Academy of Sciences of the United States of America*, 1993, 90, pp. 4304-4308.

Wang et al. "Purification and Characterization of Hypoxia-inducible Factor 1", *J Biol Chem.*,1995, 270(3), pp. 1230-1237.

Warshakoon et al., "A Novel Series of Imidazol[1,2-a]pyridine derivatives as HIF-1a prolyl hydroxylase inhibitors" *Bioorg Med Chem Lett.*, 2006, 16(21):5598-601.

Warshakoon et al., "Design and Synthesis of Substituted Pyridine Derivatives as HIF-1a Prolyl Hydroxylase Inhibitors", *Bioorg Med Chem Lett.*, 2006, 16(21):5616-20.

Wang et al "The Hypoxia Inducible Factor α Pathway Couples Angiogenesis to Osteogenesis During Skeletal Development" J Clin Invest 2007 17(6) pp. 1616-1626.

Zhu et al "Facile Preparation of Substituted Benzimidazole-2-Carboxylates" Heterocycles 2006 67(2) pp. 769-775.

Warshakoon et al., "Design and Synthesis of a Series of Novel Pyrazolopyridines as HIF 1-a prolyl hydroxylase inhibitors" *Bioorg Med Chem Lett.*, 2006, 16(21):5687-90.

Yoshida et al., "Hypoxia inducible factor 1-[alpha] regulates of platelet derived growth factor-B in human glioblastoma cells", J Neurooncol., 2006, 76(1), pp. 13-21.

Yun et al., "Inhibition of PPAR gamma 2 gene expression by the HIF-1-regulated gene DEC1/Stra13: a mechanism for regulation of adipogenesis by hypoxia." 2002, *Developmental Cell*, 2003, 2(3), pp. 331-341.

Zhang H et al. "Mitochondrial Autophagy Is an HIF-1-dependent Adaptive Metabolic Response to Hypoxia" *J Biol Chem.* 283, 2008, pp. 10892-10903.

Zou et al "Design Syhthesis and Antiviral Evaluation of 2-Chloro-5,6-dihalo-1-β-$_D$-ribofuranosylbenzimidazoles as Potential Agents for Human Cytomegalovirus Infections" J Med Chem 1997 40 pp. 811-818.

Regranex (Becaplermin) Label—Omj Pharmaceuticals Inc Revised Apr. 2010.

CAS 1017666-50-0, CAS 101766-37-3, CAS 1017666-26-0, CAS 1006582-96-2, 2010.

Rosen et al Benzimidazole-2-pyrazole HIP Prolyl 4-Hydroxylase Inhibitors as Oral Erythropoietin Secretagogues. ACS Medicinal Chemistry Letters, 2010, vol. 1 pp. 526-529.

Purpero et al"The Diverse and Pervasive Chemistries of the a-keto Acid Dependent Enzymes" J. Biol. Inorg. Chem. 2007 vol. 12 pp. 587-601.

McDonough et al "Cellular Oxygen Sensing: Crystal Structure of Hypoxia-Inducible Factor Prolyl Hydroxylase (PHD2)" PNAS 2006 vol. 103(26) pp. 9814-9819.

Wang et al "Desferrioxamine Induces Erythropoietin Gene Expression and Hypoxia-Inducible Factor 1 DNA-Binding Activity: Implications for Models of Hypoxia Signal Transduction" Blood 1993 vol. 82 pp. 3610-3615.

Tan et al "Hypoxia-Inducible Factor-1 Improves the Actions of Positive Inotropic Agents in Stunned Cardiac Myocites" Clin. Exp. Pharmacol. Physiol., 2009 vol. 36 pp. 904-911.

Dongiovanni et al "Iron Depletion by Deferoxamine Up-Regultes Glucose Uptake and Insulin Signaling in Hepatoma Cells and Rat Liver" Am. J. Pathol., 2008, 172(3) pp. 738-747.

Lee et al "Inhibition of Prolyl Hydroxylase Protects against 1-Methyl-4phenyl-1,2,3,6-tetrahydropyridine-induced Neurotoxicity" J. Biol. Chem. 2009 vol. 284 (42) pp. 29065-29076.

Ttriantafyllou et a; "Flavonoids induce HIF-1a but Impair its Nuclear Accumulation and Activity" Free Radical Biol. Med. 2008 vol. 44 pp. 657-670.

(56) References Cited

OTHER PUBLICATIONS

Park et al "Flavonoids-Induced Accumulation of Hypoxia-Inducible Factor (HIF)-1a/2a is Mediated Through Chelation of Iron" J. Cell. Biochem., 2008 vol. 103 pp. 1989-1998.
Shui et al "HIF-1: An Age-Dependent Regulator of Lens Cell Proliferation" Invest. Opthal. Vis. Sci. 2008 vol. 49(11) pp. 4961-4970.
Xia et al "Identification of Chemical Compounds that Induce HIF-1a Activity" Toxicol. Sci. 2009 vol. 112(1) pp. 153-163.
Banerji et al "The Inhibition of Factor Inhibiting Hypoxia-Inducible Factor (FIH) by B-oxocarboxylic Acids" Chem. Commun. 2005 vol. 43 pp. 5438-5440.
Cunliffe et al "Novel Inhibitors of Prolyl 4-Hydroxylase. 3. Inhibition by the Substrate Analogue N-Oxalogycine and Its Derivatives" J. Med. Chem. 1992 vol. 35 pp. 2652-2658.
Franklin et al "Approaches to the Design of Anti-fibrotic Drugs" Biochem. Soc. Trans. 1991 vol. 19 pp. 812-815.
Frohn et al "Structure-Guided Design of Substituted Aza-Benzimidazoles as Potent Hypoxia Inducible Factor-1a Prolyl Hydroxylase-2 Inhibitors" Bioorg. Med. Chem. Lett. 2008 vol. 18 pp. 5023-5026.
Tegley et al "Discovery of Novel Hydroxy-Thiazoles as HIF-a Prolyl Hydroxylase Inhibitors: SAR, Synthesis, and Modeling Evaluation" Bioorg. Med. Chem. Lett., 2008 vol. 18 pp. 3925-3928.
Vidal Juan et al 2007 Caplus an 2007:409258.
Evdokimov et al "Crystal Structure of HIF Prolyl Hydroxylase EGLN-1 in Complex with a Biologically Active Inhibitor" 2006 RCSB Protein Data Bank ID 2HBT, http://www.rcsb.org/pdb/explore.do?structureId=2hbt Accessed Dec. 30, 2013.
Hamanaka et al caplus an 1999:566034, 1999.
Smith et al Antioxidants & Reodx Signaling 210 vol. 12 pp. 431-433, 2010.
*ProlylHydroxylase* 2012 http://en.wikipedia.org/wiki/HIF_prolyl-hydroxylase_inhibitor.
*Anemia* 2012 http://www.fibrogen.com/press/release/pr_1351722380.
*Hipoxia* 2012 http://lungcancer.about.com/od/Respiratory-Symptoms/a/Hypoxia.htm.
*Bone Fracture* 2012 http://en.wikipedia.org/wiki/Bone_fracture.
STN File Registry 1017666-26-0 Apr. 27, 2008.
International search report dated Jul. 23, 2009, for international application PCT/US2009/041902.
International search report dated Jul. 3, 2009, for international application PCT/US2009/041908.
R.K. Khankari, et al., "Pharmaceutical hydrates", Thermochimica Acta 248 (1995) 61-79.
K. Sepassi, et al., "Multi-factorial approach to the development of a topical formulation of a new molecular entity", American Association of Pharmaceutical Scientists Meeting, Oct. 2011.
Hixon, L., et al., "Sizing Materials by Crushing and Grinding", Chemical Engineering, pp. 94-103 (Nov. 1990).
Parrott, E., "Milling of Pharmaceutical Solids", Journal of Pharmaceutical Sciences, vol. 63, No. 6, pp. 813-829 (Jun. 1974).
Perry's Chemical Engineers' Handbook, 6$^{th}$ Ed., "Introduction to Screening and Wet Classification", pp. 21.13-21.19 (1984).
International Search Report and Written Opinion dated Nov. 26, 2012, for Corresponding International Application PCT/EP2012/061847.

* cited by examiner

Compound 1

| Properties | Values |
|---|---|
| pKa | 3.67 and 8.57 (exp.) |
| log $D_{7.4}$ | 0.28 (exp.) |
| MW | 297.10 |

A

B

Simulated powder pattern (Mercury 2.3)

Remove Egg Membrane    Treatment

MEGLUMINE SALT FORMULATIONS OF 1-(5,6-DICHLORO-1H-BENZO[D]IMIDAZOL-2-YL)-1H-PYRAZOLE-4-CARBOXYLIC ACID

CROSS REFERENCE TO RELATED APPLICATION

This application is a national stage of PCT Application PCT/US2012/061847, filed Oct. 25, 2012, which claims priority to application U.S. 61/551,395, filed on Oct. 25, 2011.

FIELD OF THE INVENTION

The present invention is directed to the meglumine salt of 1-(5,6-dichloro-1H-benzo[d]imidazol-2-yl)-1H-pyrazole-4-carboxylic acid and related methods of manufacture.

BACKGROUND

A family of highly conserved oxygen, iron, and 2-oxoglutarate-dependent prolyl hydroxylase (PHD) enzymes mediate the cells response to hypoxia via post-translational modification of hypoxia-inducible factors (HIF) (Ivan et al., 2001, *Science*, 292:464-68; Jaakkola et al., 2001, *Science*, 292:468-72). Under normoxic conditions, PHD catalyzes the hydroxylation of two conserved proline residues within HIF. As the affinity of PHD for oxygen is within the physiological range of oxygen and oxygen is a necessary co-factor for modifying hydroxylated HIF, PHD is inactivated when oxygen tension is reduced. In this way, HIF is rapidly degraded under normoxic conditions but accumulates in cells under hypoxic conditions or when PHD is inhibited.

Four isotypes of PHD have been described: PHD1, PHD2, PHD3, and PHD4 (Epstein et al., 2001, *Cell*, 107:43-54; Kaelin, 2005, *Annu Rev Biochem.*, 74:115-28; Schmid et al., 2004, *J Cell Mol Med.*, 8:423-31). The different isotypes are ubiquitously expressed but are differentially regulated and have distinct physiological roles in the cellular response to hypoxia. There is evidence that the various isotypes have different selectivity for the three different HIF-α sub-types (Epstein et al., supra). In terms of cellular localization, PHD1 is primarily nuclear, PHD2 is primarily cytoplasmic, and PHD3 appears to be both cytoplasmic and nuclear (Metzen E, et al. 2003, *J Cell Sci.*, 116(7):1319-26). PHD2 appears to be the predominant HIF-α prolyl hydroxylase under normoxic conditions (Ivan et al., 2002. *Proc Natl Acad USA*, 99(21): 13459-64; Berra et al., 2003, *EMBO J.*, 22:4082-90). The three isotypes have a high degree of amino-acid homology and the active site of the enzyme is highly conserved.

Targeted disruption of the PHD enzyme activity by small molecules has potential utility in the treatment of disorders of oxygen sensing and distribution. Examples include but are not limited to: anemia; sickle cell anemia; peripheral vascular disease; coronary artery disease; heart failure; protection of tissue from ischemia in conditions such as myocardial ischemia, myocardial infarction and stroke; preservation of organs for transplant; treatment of tissue ischemia by regulating and/or restoring blood flow, oxygen delivery and/or energy utilization; acceleration of wound healing particularly in diabetic and aged patients; treatment of burns; treatment of infection; bone healing, and bone growth. In addition, targeted disruption of PHD is expected to have utility in treating metabolic disorders such as diabetes, obesity, ulcerative colitis, inflammatory bowel disease and related disorders such as Crohn's disease. (*Recent Patents on Inflammation & Allergy Drug Discovery*, 2009, 3:1-16).

HIF has been shown to be the primary transcriptional factor that leads to increased erythropoietin production under conditions of hypoxia (Wang et al., 1993, supra). While treatment with recombinant human erythropoietin has been demonstrated to be an effective method of treating anemia, small molecule mediated PHD inhibition can be expected to offer advantages over treatment with erythropoietin. Specifically, the function of other HIF gene products is necessary for hematopoesis and regulation of these factors increases the efficiency of hematopoesis. Examples of HIF target gene products that are critical for hematopoesis include: transferrin (Rolfs et al., 1997, *J Biol Chem.*, 272(32):20055-62), transferrin receptor (Lok et al., 1999, *J Biol Chem.*, 274(34): 24147-52; Tacchini et al., 1999, *J Biol Chem.*, 274(34):24142-46) and ceruloplasmin (Mukhopadhyay et al., 2000, *J Biol Chem.*, 275(28):21048-54). Hepcidin expression is also suppressed by HIF (Peyssonnaux et al., 2007, *J Clin Invest.*, 117(7):1926-32) and small molecule inhibitors of PHD have been shown to reduce hepcidin production (Braliou et al., 2008, *J Hepatol.*, 48:801-10). Hepcidin is a negative regulator of the availability of the iron that is necessary for hematopoesis, so a reduction in hepcidin production is expected to be beneficial to the treatment of anemia. PHD inhibition may also be useful when used in conjunction with other treatments for anemia including iron supplementation and/or exogenous erythropoietin. Studies of mutations in the PHD2 gene occurring naturally in the human population provide further evidence for the use of PHD inhibitors to treat anemia. Two recent reports have shown that patients with dysfunctional mutations in the PHD2 gene display increased erythrocytosis and elevated blood hemoglobin (Percy et al., 2007, *PNAS*, 103(3):654-59; Al-Sheikh et al., 2008, *Blood Cells Mol Dis.*, 40:160-65). In addition, a small molecule PHD inhibitor has been evaluated in healthy volunteers and patients with chronic kidney disease (U.S. Pat. App. No. US2006/0276477, Dec. 7, 2006). Plasma erythropoietin was increased in a dose-dependent fashion and blood hemoglobin concentrations were increased in the chronic kidney disease patients.

Overall accumulation of HIF under hypoxic conditions governs an adaptive up-regulation of glycolysis, a reduction in oxidative phosphorylation resulting in a reduction in the production of hydrogen peroxide and superoxide, optimization of oxidative phosphorylation protecting cells against ischemic damage. Thus, PHD inhibitors are expected to be useful in organ and tissue transplant preservation (Bernhardt et al., 2007, *Methods Enzymol.*, 435:221-45). While benefit may be achieved by administering PHD inhibitors before harvesting organs for transplant, administration of an inhibitor to the organ/tissue after harvest, either in storage (e.g., cardioplegia solution) or post-transplant, may also be of therapeutic benefit.

PHD inhibitors are expected to be effective in preserving tissue from regional ischemia and/or hypoxia. This includes ischemia/hypoxia associated with inter alia: angina, myocardial ischemia, stroke, ischemia of skeletal muscle. Recently, ischemic pre-conditioning has been demonstrated to be a HIF-dependent phenomenon (Cai et al., 2008, *Cardiovasc Res.*, 77(3):463-70). While the concept of pre-conditioning is best known for its protective effects in the heart, it also applies to other tissues including but not limited to: liver, skeletal muscle, liver, lung, kidney, intestine and brain (Pasupathy et al., 2005, *Eur J Vasc Endovasc Surg.*, 29:106-15; Mallick et al., 2004, *Dig Dis Sci.*, 49(9):1359-77). Experimental evidence for the tissue protective effects of PHD inhibition and elevation of HIF have been obtained in a number of animal models including: germ-line knock out of PHD1 which conferred protection of the skeletal muscle from ischemic insult (Aragonés et al., 2008, *Nat Genet.*, 40(2):170-80), silencing of PHD2 through the use of siRNA which protected the heart from ischemic insult (Natarajan et al., 2006, *Circ Res.*, 98(1): 133-40), inhibition of PHD by administering carbon monoxide which protected the myocardium from ischemic injury (Chin et al., 2007, *Proc Natl Acad Sci. U.S.A.*, 104(12):5109-14), hypoxia in the brain which increased the tolerance to ischemia (Bernaudin et al., 2002, *J Cereb Blood Flow Metab.*, 22(4):393-403). In addition, small molecule inhibitors of PHD protect the brain in experimental stroke models (Siddiq et al., 2005, *J Biol Chem.*, 280(50):41732-43). Moreover, HIF up-regulation has also been shown to protect the heart of diabetic mice, where outcomes are generally worse (Natarajan et al., 2008, *J Cardiovasc Pharmacol.*, 51(2):178-187). The tissue protective effects may also be observed in Buerger's disease, Raynaud's disease, and acrocyanosis.

The reduced reliance on aerobic metabolism via the Kreb's cycle in the mitochondria and an increased reliance on anaerobic glycolysis produced by PHD inhibition may have beneficial effects in normoxic tissues. It is important to note that PHD inhibition has also been shown to elevate HIF under normoxic conditions. Thus, PHD inhibition produces a pseudohypoxia associated with the hypoxic response being initiated through HIF but with tissue oxygenation remaining normal. The alteration of metabolism produced by PHD inhibition can also be expected to provide a treatment paradigm for diabetes, obesity and related disorders, including co-morbidities.

Globally, the collection of gene expression changes produced by PHD inhibition reduce the amount of energy generated per unit of glucose and will stimulate the body to burn more fat to maintain energy balance. The mechanisms for the increase in glycolysis are discussed above. Other observations link the hypoxic response to effects that are expected to be beneficial for the treatment of diabetes and obesity. Hypoxia and hypoxia mimetics such as desferrioxamine have been shown to prevent adipocyte differentiation (Lin et al., 2006, *J Biol Chem.*, 281(41):30678-83; Carrière et al., 2004, *J Biol Chem.*, 279(39):40462-69). Inhibition of PHD activity during the initial stages of adipogenesis inhibits the formation of new adipocytes (Floyd et al., 2007, *J Cell Biochem.*, 101: 1545-57). Hypoxia, cobalt chloride and desferrioxamine elevated HIF and inhibited PPAR gamma 2 nuclear hormone receptor transcription (Yun et al., 2002, *Dev Cell.*, 2:331-41). As PPAR gamma 2 is an important signal for adipocyte differentiation, PHD inhibition can be expected to inhibit adipocyte differentiation. These effects were shown to be mediated by the HIF-regulated gene DEC1/Stra13 (Yun et al., supra).

Small molecular inhibitors of PHD have been demonstrated to have beneficial effects in animal models of diabetes and obesity (Intl. Pat. App. Pub. No. WO2004/052284, Jun. 24, 2004; WO2004/052285, Jun. 24, 2004). Among the effects demonstrated for PHD inhibitors in mouse diet-induced obesity, db/db mouse and Zucker fa/fa rat models were lowering of: blood glucose concentration, fat mass in both abdominal and visceral fat pads, hemoglobin A1c, plasma triglycerides, body weight as well as changes in established disease bio-markers such as increases in the levels of adrenomedullin and leptin. Leptin is a known HIF target gene product (Grosfeld et al., 2002, *J Biol Chem.*, 277(45):42953-57). Gene products involved in the metabolism in fat cells were demonstrated to be regulated by PHD inhibition in a HIF-dependent fashion (Intl. Pat. App. Pub. No. WO2004/ 052285, supra). These include apolipoprotein A-IV, acyl CoA thioesterase, carnitine acetyl transferase, and insulin-like growth factor binding protein (IGFBP)-1.

PHD inhibitors are expected to be therapeutically useful as stimulants of vasculogenesis, angiogenesis, and arteriogenesis. These processes establish or restore blood flow and oxygenation to the tissues under ischemia and/or hypoxia conditions (Semenza et al., 2007, *J Cell Biochem.*, 102:840-47; Semenza, 2007, *Exp Physiol.*, 92(6):988-91). It has been shown that physical exercise increases HIF-1 and vascular endothelial growth factor in experimental animal models and in humans (Gustafsson et al. 2001, *Front Biosci.*, 6:D75-89) and consequently the number of blood vessels in skeletal muscle. VEGF is a well-known HIF target gene product that is a key driver of angiogenesis (Liu et al., supra). PHD inhibition offers a potential advantage over other angiogenic therapies in that it stimulates a controlled expression of multiple angiogenic growth factors in a HIF-dependent fashion including but not limited to: placental growth factor (PLGF), angiopoietin-1 (ANGPT1), angiopoietin-2 (ANGPT2), platelet-derived growth factor beta (PDGFB) (Carmeliet, 2004, *J Intern Med.*, 255:538-61; Kelly et al., 2003, *Circ Res.*, 93:1074-81) and stromal cell derived factor 1 (SDF-1) (Ceradini et al., 2004, *Nat Med.*, 10(8):858-64). Expression of angiopoietin-1 during angiogenesis produces leakage-resistant blood vessels, in contrast to the vessels produced by administration of VEGF alone (Thurston et al., 1999, *Science*, 286:2511-14; Thurston et al., 2000, *Nat Med.*, 6(4):460-3; Elson et al., 2001, *Genes Dev.*, 15(19):2520-32). Stromal cell derived factor 1 (SDF-1) has been shown to be critical to the process of recruiting endothelial progenitor cells to the sites of tissue injury. SDF-1 expression increased the adhesion, migration and homing of circulating CXCR4-positive progenitor cells to ischemic tissue. Furthermore inhibition of SDF-1 in ischemic tissue or blockade of CXCR4 on circulating cells prevents progenitor cell recruitment to sites of injury (Ceradini et al., 2004, supra; Ceradini et al., 2005, *Trends Cardiovasc Med.*, 15(2):57-63). Importantly, the recruitment of endothelial progenitor cells to sites of injury is reduced in aged mice and this is corrected by interventions that increase HIF at the wound site (Chang et al., 2007, *Circulation*, 116 (24):2818-29). PHD inhibition offers the advantage not only of increasing the expression of a number of angiogenic factions but also a co-ordination in their expression throughout the angiogenesis process and recruitment of endothelial progenitor cells to ischemic tissue.

PHD inhibitors are useful in pro-angiogenic therapies, too. Adenovirus-mediated over-expression of HIF has been demonstrated to induce angiogenesis in non-ischemic tissue of an adult animal (Kelly et al., 2003, *Circ Res.*, 93(11):1074-81) providing evidence that therapies that elevate HIF, such as PHD inhibition, will induce angiogenesis. Placental growth factor (PLGF), also a HIF target gene, has been show to play a critical role in angiogenesis in ischemic tissue (Carmeliet, 2004, *J Intern Med.*, 255(5):538-61; Luttun et al., 2002, *Ann N Y Acad Sci.*, 979:80-93). The potent pro-angiogenic effects of therapies that elevate HIF have been demonstrated, via HIF over-expression, in skeletal muscle (Pajusola et al., 2005, *FASEB J.*, 19(10):1365-7; Vincent et al., 2000, *Circulation*, 102:2255-61) and in the myocardium (Shyu et al., 2002, *Cardiovasc Res.*, 54:576-83). The recruitment of endothelial progenitor cells to the ischemic myocardium by the HIF target gene SDF-1 has also been demonstrated (Abbott et al., 2004, *Circulation*, 110(21):3300-05). Thus, PHD inhibitors will likely be effective in stimulating angiogenesis in the setting of tissue ischemia, particularly muscle ischemia. Therapeutic angiogenesis produced by PHD inhibitors will likely lead to restoring blood flow to tissues and therefore meliorate such diseases as but not limited to angina pectoris, myocardial ischemia and infarction, peripheral ischemic disease, claudication, gastric and duodenal ulcers, ulcerative colitis, and inflammatory bowel disease.

PHD and HIF play a central role in tissue repair and regeneration including healing of wounds and ulcers. Recent studies have demonstrated that an increased expression of all three PHDs at wound sites in aged mice with a resulting reduction in HIF accumulation (Chang et al., supra). Thus, elevation of HIF in aged mice by administering desferrioxamine increased the degree of wound healing back to levels observed in young mice. Similarly, in a diabetic mouse model, HIF elevation was suppressed compared to non-diabetic litter mates (Mace et al., 2007, *Wound Repair Regen.*, 15(5):636-45). Topical administration of cobalt chloride, a hypoxia mimetic, or over-expression of a murine HIF that lacks the oxygen-dependent degradation domain and thus provides for a constitutively active form of HIF, resulted in increased HIF at the wound site, increased expression of HIF target genes such as VEGF, Nos2, and Hmox1 and accelerated wound healing. The beneficial effect of PHD inhibition is not restricted to the skin and small molecule inhibitors of PHD have recently been demonstrated to provide benefit in a mouse model of colitis (Robinson et al., 2008, *Gastroenterology*, 134(1):145-55).

In summary, PHD inhibition resulting in accumulation of HIF likely acts by at least four mechanisms to contribute to accelerated and more complete healing of wounds: 1) protection of tissue jeopardized by hypoxia and/or ischemia, 2) stimulation of angiogenesis to establish or restore appropriate blood flow to the site, 3) recruitment of endothelial progenitor cells to wound sites, 4) stimulation of the release of growth factors that specifically stimulate healing and regeneration.

As PDGF is a HIF gene target (Schultz et al., 2006, *Am J Physiol Heart Circ Physiol.*, 290(6):H2528-34;Yoshida et al., 2006, *J Neurooncol.*, 76(1):13-21), PHD inhibition likely increases the expression of endogenous PDGF and produces a similar or more beneficial effect to those produced with PDGF alone. Studies in animals have shown that topical application of PDGF results in increased wound DNA, protein, and hydroxyproline amounts; formation of thicker granulation and epidermal tissue; and increased cellular repopulation of wound sites. PDGF exerts a local effect on enhancing the formation of new connective tissue. The effectiveness of PHD inhibition is likely greater than that produced by PDGF due to the additional tissue protective and pro-angiogenic effects mediated by HIF.

The beneficial effects of inhibition of PHD extends not only to accelerated wound healing in the skin and colon but also to the healing of other tissue damage including but not limited to gastrointestinal ulcers, skin graft replacements, burns, chronic wounds and frost bite.

Stem cells and progenitor cells are found in hypoxic niches within the body and hypoxia regulates their differentiation and cell fate (Simon et al., 2008, *Nat Rev Mol Cell Biol.*, 9:285-96). Thus, PHD inhibitors may be useful to maintain stem cells and progenitor cells in a pluripotent state and to drive differentiation to desired cell types. Stem cells may be useful in culturing and expanding stem cell populations and may hold cells in a pluripotent state while hormones and other factors are administered to the cells to influence the differentiation and cell fate.

A further use of PHD inhibitors in the area of stem cell and progenitor cell therapeutics relates to the use of PHD inhibitors to condition these cells to withstand the process of implantation into the body and to generate an appropriate response to the body to make the stem cell and progenitor cell implantation viable (Hu et al., 2008, *J Thorac Cardiovasc Surg.*, 135(4):799-808). More specifically PHD inhibitors may facilitate the integration of stem cells and draw in an appropriate blood supply to sustain the stem cells once they are integrated. This blood vessel formation will also function to carry hormones and other factors released from these cells to the rest of the body.

PHD inhibitors may also be useful in the treatment of infection (Peyssonnaux et al., 2005, *J Invest Dermatol.*, 115 (7):1806-15; Peyssonnaux et al., 2008 *J Invest Dermatol.*, 2008 August; 128(8):1964-8). HIF elevation has been demonstrated to increase the innate immune response to infection in phagocytes and in keratinocytes. Phagocytes in which HIF is elevated show increased bacteriacidal activity, increased nitric oxide production and increased expressed of the antibacterial peptide cathelicidin. These effects may also be useful in treating infection from burns.

HIF has also been shown to be involved in bone growth and healing (Pfander D et al., 2003 *J Cell Sci.*, 116(Pt 9):1819-26., Wang et al., 2007 *J Clin Invest.*, 17(6):1616-26.) and may therefore be used to heal or prevent fractures. HIF stimulates of glycolysis to provide energy to allow the synthesis of extracellular matrix of the epiphyseal chondrocytes under a hypoxic environment. HIF also plays a role in driving the release of VEGF and angiogenesis in bone healing process. The growth of blood vessels into growing or healing bone can be the rate limiting step in the process.

Small molecules inhibitors of PHD have been described in the literature, which include, but are not limited to, imidazo [1,2-a]pyridine derivatives (Warshakoon et al., 2006, *Bioorg Med Chem Lett.*, 16(21):5598-601), substituted pyridine derivatives (Warshakoon et al., 2006, *Bioorg Med Chem Lett.*, 16(21):5616-20), pyrazolopyridines (Warshakoon et al., 2006, *Bioorg Med Chem Lett.*, 16(21):5687-90), bicyclic heteroaromatic N-substituted glycine derivatives (Intl. Pat. App. Pub. No. WO2007/103905, Sep. 13, 2007), quinoline based compounds (Intl. Pat. App. Pub. No. WO2007/070359, Jun. 21, 2007), pyrimidinetrione N-substituted glycine derivatives (Intl. Pat. App. Pub. No. WO2007/150011, Dec. 27, 2007), substituted aryl or heteroaryl amide compounds (U.S. Pat. App. Pub. No. US 2007/0299086, Dec. 27, 2007) and substituted 4-hydroxypyrimidine-5-carboxamides (Intl. Pat. App. Pub. No. WO2009/117269, Sep. 24, 2009).

SUMMARY OF THE INVENTION

The invention is directed to the general and preferred embodiments defined, as set forth herein. Preferred and exemplary features of the invention will be apparent from the detailed description below and with reference to the drawing figures.

In its many embodiments, the present invention relates to a novel salt of an inhibitor of prolyl hydroxylase (PHD) enzymes, and a method of treatment, prevention, inhibition or amelioration of one or more diseases disorders associated with PHD enzymes is provided.

More particularly, the present invention relates to the meglumine salt of a compound of the following formula:

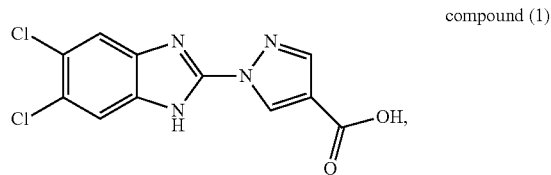 [SMILES: O=C(O)c1cnn(-c2nc3cc(Cl)c(Cl)cc3[nH]2)c1]

compound (1)

and related methods of preparation or manufacture of the compound.

In another embodiment, the present invention relates to the hydrated form of the meglumine salt of compound (1).

Additional embodiments and advantages of the invention will become apparent from the detailed discussion, schemes, examples, and claims below.

DETAILED DESCRIPTION OF THE INVENTION

Figure 1:
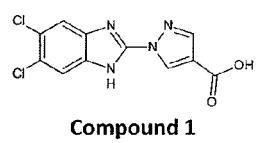
FIG. 1 shows the pH-dependency of saturation of compound (1) in solution.
Figure 1:
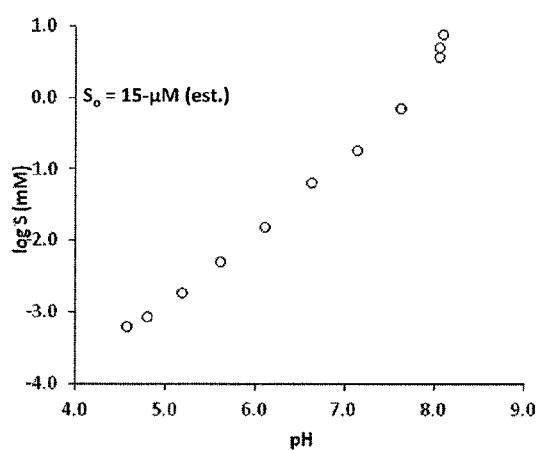

This invention relates to a novel salt of a compound of the following formula:

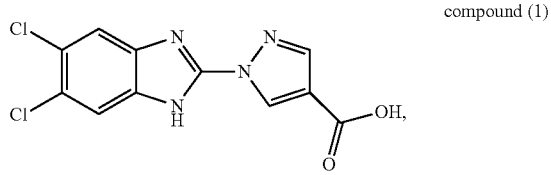 [SMILES: O=C(O)c1cnn(-c2nc3cc(Cl)c(Cl)cc3[nH]2)c1]

compound (1)

that is a inhibitor of prolyl hydroxylase (PHD) enzymes, and compositions thereof for the treatment, amelioration or inhibition of disorders and diseases related to the modulation of a prolyl hydroxylase enzyme. The present invention also relates to methods of making such a compound, pharmaceutical compositions, pharmaceutically acceptable salts, pharmaceutically acceptable prodrugs, and pharmaceutically active metabolites thereof.

A) Terms

The present invention is best understood by reference to the following definitions, the drawings and exemplary disclosure provided herein.

The terms "comprising", "containing", and "including," are used herein in their open, non-limiting sense.

"Administering" or "administration" means providing a drug to a patient in a manner that is pharmacologically useful.

"Composition" means a product containing a compound of the present invention (such as a product comprising the specified ingredients in the specified amounts, as well as any product which results, directly or indirectly, from such combinations of the specified ingredients in the specified amounts).

"Compound" or "drug" means a compound of Formula (1) or pharmaceutically acceptable forms thereof.

"Forms" means various isomers and mixtures of one or more compounds of Formula (1) and salts or hydrates thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers). The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry.

The term "hypoxia" or "hypoxic disorder" refers to a condition where there is an insufficient level of oxygen provided in the blood or to tissues and organs. Hypoxic disorders can occur through a variety of mechanisms including where there is an insufficient capacity of the blood to carry oxygen (i.e. anemia), where there is an inadequate flow of blood to the tissue and/or organ caused by either heart failure or blockage of blood vessels and/or arteries (i.e. ischemia), where there is reduced barometric pressure (i.e. elevation sickness at high altitudes), or where dysfunctional cells are unable to properly make use of oxygen (i.e. hystotoxic conditions). Accordingly, one of skill in the art would readily appreciate the present invention to be useful in the treatment of a variety of hypoxic conditions including anemia, heart failure, coronary artery disease, thromboembolism, stroke, angina and the like.

"Patient" or "subject" means an animal, preferably a mammal, more preferably a human, in need of therapeutic intervention.

"Pharmaceutically acceptable" means molecular entities and compositions that are of sufficient purity and quality for use in the formulation of a composition or medicament of the present invention. Since both human use (clinical and over-the-counter) and veterinary use are equally included within the scope of the present invention, a formulation would include a composition or medicament for either human or veterinary use.

"Pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Pharmaceutically acceptable salt" means an acid or base salt of the compounds of the invention that is of sufficient purity and quality for use in the formulation of a composition or medicament of the present invention and are tolerated and sufficiently non-toxic to be used in a pharmaceutical preparation. Suitable pharmaceutically acceptable salts include acid addition salts which may, for example, be formed by reacting the drug compound with a suitable pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

The term "solvates" means those compounds that are formed from the interaction or complexation of such compounds with one or more solvent molecule, either in solution or in solid or crystalline form. The term "hydrates" mean solvates, wherein the solvent is water.

"Therapeutically effective amount" means that amount of compound that elicits the biological or medicinal response in a tissue system, animal or human, that is being sought by a researcher, veterinarian, medical doctor, or other clinician, which includes therapeutic alleviation of the symptoms of the disease or disorder being treated.

The term "treating" as used herein, unless otherwise indicated, means reversing, alleviating, inhibiting the progress of, lessening the severity of, or preventing the disorder or condition to which such term applies, or one or more symptoms of such disorder or condition. The term "treatment", as used herein, unless otherwise indicated, refers to the act of treating.

B) Compounds

The present invention relates to novel salts of compound of Formula (1). In particular, the invention relates to the meglumine salt of compound of Formula (1). In general, the invention relates to all compounds that upon administration to patients in need of treatment of disorders and diseases related to the modulation of a prolyl hydroxylase enzyme.

Some embodiments of the invention include hydrates, solvates or polymorphs of such compounds, and mixtures thereof, even if such forms are not explicitly stated in the present specification. Preferably, some embodiments of compounds of Formula (1) or pharmaceutically acceptable salts thereof include solvates. More preferably, some embodiments of compounds of Formula (1) or pharmaceutically acceptable salts thereof include hydrates.

Yet another embodiment of the invention includes crystalline forms of compounds of Formula (1) or pharmaceutically acceptable salts of compounds of Formula (1) may be obtained as co-crystals.

In certain embodiments of the invention, compounds of Formula (1) were obtained in a crystalline form. In other embodiments, crystalline forms of compounds of Formula (1) were cubic in nature. In other embodiments, pharmaceutically acceptable salts of compounds of Formula (1) were obtained in a crystalline form. In still other embodiments, compounds of Formula (1) were obtained in one of several polymorphic forms, as a mixture of crystalline forms, as a polymorphic form, or as an amorphous form. In other embodiments, compounds of Formula (1) convert in solution between one or more crystalline forms and/or polymorphic forms.

Drug compounds of the present invention also include a mixture of stereoisomers, or each pure or substantially pure isomer. For example, the present compound may optionally have one or more asymmetric centers at a carbon atom containing any one substituent. Therefore, the compound may exist in the form of enantiomer or diastereomer, or a mixture thereof. When the present compound contains a double bond, the present compound may exist in the form of geometric isomerism (cis-compound, trans-compound), and when the present compound contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization. In addition, the present compound includes an intramolecular salt, hydrate, solvate or polymorphism thereof. Suitable drug compounds are those that exert a local physiological effect, or a systemic effect, either after penetrating the mucosa, dermis or—in the case of oral administration—after transport to the gastrointestinal tract with saliva.

The invention further relates to pharmaceutically acceptable salts of compounds of Formula (1) and methods of using such salts. A pharmaceutically acceptable salt refers to a salt of a free acid or base of the compound that is non-toxic, biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, 2002, Stahl and Wermuth, Eds., Wiley-VCH and VHCA, Zurich. Preferred pharmaceutically acceptable salts are those that are pharmacologically effective and suitable for contact with the tissues of patients without undue toxicity, irritation, or allergic response. A compound may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenyl butyrates, citrates, lactates, γ-hydroxybutyrates, glycolates, tartrates, methane-sulfonates, propanesulfonates, naphthalene-1-sulfonates, naphthalene-2-sulfonates, and mandelates.

In the presence of a basic nitrogen, the desired pharmaceutically acceptable salt may be prepared by any suitable method available in the art, for example, treatment of the free base with an inorganic acid, such as hydrochloric acid, hydrobromic acid, hydriodic acid, perchloric acid, sulfuric acid, sulfamic acid, nitric acid, boric acid, phosphoric acid, and the like, or with an organic acid, such as acetic acid, trifluoroacetic acid, phenylacetic acid, propionic acid, stearic acid, lactic acid, ascorbic acid, maleic acid, hydroxymaleic acid, malic acid, pamoic acid, isethionic acid, succinic acid, valeric acid, fumaric acid, saccharinic acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, benzenesulfonic acid, 2-naphthalenesulfonic acid, p-toluenesulfonic acid, methanesulfonic acid, ethanesulfonic acid, hydroxyethanesulfonic, a cyclohexanesulfamic acid, any compatible mixture of acids such as those given as examples herein, and any other acid and mixture thereof that are regarded as equivalents or acceptable substitutes in light of the ordinary level of skill in this technology.

In the presence of an acid group, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium. Representative organic or inorganic bases further include benzathine, chloroprocaine, choline, diethanolamine, ethylenediamine, meglumine, and procaine.

The invention also relates to pharmaceutically acceptable prodrugs of the compounds, and treatment methods employing such pharmaceutically acceptable prodrugs. The term "prodrug" means a precursor of a designated compound that, following administration to a subject yields the compound in vivo via a chemical or physiological process such as solvolysis or enzymatic cleavage, or under physiological conditions. A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, 1985, Elsevier.

Additional types of prodrugs may be produced, for instance, by derivatizing free carboxyl groups of structures of the compound as amides or alkyl esters. Examples of amides include those derived from ammonia, primary alkyl amines and secondary di-alkyl amines. Secondary amines include 5- or 6-membered heterocycloalkyl or heteroaryl ring moieties. Examples of amides include those that are derived from ammonia, alkyl primary amines, and di-alkyl amines. Examples of esters of the invention include alkyl, cycloalkyl, phenyl, and phenyl-alkyl esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.*, 1996, 19:115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as acyloxy-methyl and acyloxy-ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Greenwald, et al., *J. Med. Chem.*, 1996, 39 (10):1938-40. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (1), which may also be used in the methods of the invention. A "pharmaceutically active metabolite" means a pharmacologically active product of metabolism in the body of the compound or salt thereof. Prodrugs and active metabolites of a compound may be determined using routine techniques known or available in the art. See, e.g., Bertolini, et al., *J. Med. Chem.*, 1997, 40:2011-2016; Shan, et al., *J. Pharm. Sci.*, 1997, 86 (7):765-767; Bagshawe, *Drug Dev. Res.*, 1995, 34:220-230; Bodor, *Adv. Drug Res.*, 1984, 13:224-331; Bundgaard, Design of Prodrugs, 1985, Elsevier Press; and Larsen, Design and Application of Prodrugs, Drug Design and Development, 1991, Krogsgaard-Larsen, et al., eds., Harwood Academic Publishers.

C) Pharmaceutical Compositions

In particular embodiments of the invention, the salts of compounds of Formula (1), more particularly the meglumine salt, are used alone, or in combination with one or more additional ingredients, to formulate pharmaceutical compositions. A pharmaceutical composition comprises an effective amount of at least one compound in accordance with the invention.

The disclosure also provides compositions (including pharmaceutical compositions) comprising a compound or derivatives described herein, and one or more of pharmaceutically acceptable carrier, excipient, and diluent. In certain embodiments of the invention, a composition may also contain minor amounts of wetting or emulsifying agents, or pH buffering agents. In a specific embodiment, the pharmaceutical composition is pharmaceutically acceptable for administration to a human. In certain embodiments, the pharmaceutical composition comprises a therapeutically or prophylactically effective amount of a compound or derivative described herein. The amount of a compound or derivative of the invention that will be therapeutically or prophylactically effective can be determined by standard clinical techniques. Exemplary effective amounts are described in more detail in below sections. In certain embodiments of the invention, a composition may also contain a stabilizer. A stabilizer is a compound that reduces the rate of chemical degradation of the composition of compound (1). Suitable stabilizers include, but are not limited to, antioxidants, such as ascorbic acid, pH buffers, or salt buffers.

The pharmaceutical compositions can be in any form suitable for administration to a subject, preferably a human subject. In certain embodiments, the compositions are in the form of solutions, suspensions, emulsion, tablets, pills, capsules, powders, and sustained-release formulations. The compositions may also be in particular unit dosage forms. Examples of unit dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

In a specific embodiment, the subject is a mammal such as a cow, horse, sheep, pig, fowl, cat, dog, mouse, rat, rabbit, or guinea pig. In a preferred embodiment, the subject is a human. Preferably, the pharmaceutical composition is suitable for veterinary and/or human administration. In accordance with this embodiment, the term "pharmaceutically acceptable" means approved by a regulatory agency of the Federal or a state government or listed in the U.S. Pharmacopeia or other generally recognized pharmacopeia for use in animals, and more particularly for use in humans.

Suitable pharmaceutical carriers for use in the compositions are sterile liquids, such as water and oils, including those of petroleum, animal, vegetable or synthetic origin. In a specific embodiment, the oil is peanut oil, soybean oil, mineral oil, or sesame oil. Water is a preferred carrier when the pharmaceutical composition is administered intravenously. Saline solutions and aqueous dextrose and glycerol solutions can also be employed as liquid carriers, particularly for injectable solutions. Further examples of suitable pharmaceutical carriers are known in the art, e.g., as described in Remington's Pharmaceutical Sciences (1990) 18th ed. (Mack Publishing, Easton Pa.).

Suitable excipients for use in the compositions include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. Whether a particular excipient is suitable for incorporation into a pharmaceutical composition depends on a variety of factors well known in the art including, but not limited to, the route of administration and the specific active ingredients in the composition.

Pharmaceutical compositions comprising the compounds or derivatives described herein, or their pharmaceutically acceptable salts and solvates, are formulated to be compatible with the intended route of administration. The formulations are preferably for topical administration, but can be for administration by other means such as by inhalation or insufflation (either through the mouth or the nose), intradermal, oral, subcutaneous, buccal, parenteral, vaginal, or rectal. Preferably, the compositions are also formulated to provide increased chemical stability of the compound during storage and transportation. The formulations may be lyophilized or liquid formulations.

D) Administration

A compound or derivative described herein, or a pharmaceutically acceptable salt thereof, is preferably administered as a component of a composition that optionally comprises a pharmaceutically acceptable vehicle. The compound or derivative is preferably administered orally. Another preferred method of administration is via topical application of the compound or derivative.

In certain embodiments, the compound or derivative is administered by any other convenient route, for example, by absorption through skin, epithelial or mucocutaneous linings (e.g., (epi-)dermis, oral mucosa, rectal, and intestinal mucosa). Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In most instances, administration will result in the release of the compound or derivative into the bloodstream. In preferred embodiments, the compound or derivative is delivered orally.

Furthermore, the invention relates to methods of using the compounds described herein to treat subjects diagnosed with or suffering from a disease, disorder, or condition mediated by prolyl hydroxylase, such as: anemia, vascular disorders, metabolic disorders, and wound healing.

In a preferred embodiment, compounds of the present invention are useful in the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosteroid hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD inhibition may also be used to treat symptoms of anemia including chronic fatigue, pallor and dizziness.

In another preferred embodiment, molecules of the present invention are useful for the treatment or prevention of diseases of metabolic disorders, including but not limited to diabetes and obesity. In another preferred embodiment, molecules of the present invention are useful for the treatment or prevention of vascular disorders. These include but are not limited to hypoxic or wound healing related diseases requiring pro-angiogenic mediators for vasculogenesis, angiogenesis, and arteriogenesis In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Examples include lotions, creams, ointments and the like and can be formulated by known methods. Another mode of administering the compounds of the invention may utilize a patch formulation to affect transdermal delivery.

A salt-selection evaluation was carried to identify a salt of compound (1) with properties most suitable for development. The criteria considered essential for the selection process were crystallinity, form reproducibility from a recrystallization process, chemical and physical stability under accelerated conditions and adequate solubility to support both drug substance and drug product development.

In embodiments, the compound is formulated into dosage forms suitable for administration to patients in need thereof. The processes and equipment for preparing drug and carrier particles are disclosed in Pharmaceutical Sciences, Remington, 1985, 17th Ed., 1585-1594; Chemical Engineers Handbook, Perry, 1984, 6th Ed., pp. 21-13 to 21-19 (1984); Parrot et al., 1974, *J. Pharm. Sci.*, 61(6): 813-829; and Hixon et al., 1990, *Chem. Engineering*, pp. 94-103.

The amount of compound incorporated in the dosage forms of the present invention may generally vary from about 10% to about 90% by weight of the composition depending upon the therapeutic indication and the desired administration period, e.g., every 12 hours, every 24 hours, and the like. Depending on the dose of compound desired to be administered, one or more of the dosage forms can be administered. Depending upon the formulation, the compound will preferably be in the form of an acetate salt or free base form.

Further, this invention also relates to a pharmaceutical composition or a pharmaceutical dosage form as described hereinbefore for use in a method of therapy or diagnosis of the human or non-human animal body.

This invention also relates to a pharmaceutical composition for use in the manufacture of a pharmaceutical dosage form for oral administration to a mammal in need of treatment, characterized in that said dosage form can be administered at any time of the day independently of the food taken in by said mammal.

This invention also relates to a method of therapy or diagnosis of the human or non-human animal body that comprises administering to said body a therapeutically or diagnostically effective dose of a pharmaceutical composition described herein.

This invention also relates to a pharmaceutical package suitable for commercial sale comprising a container, a dosage form as described herein, and associated with said package written matter non-limited as to whether the dosage form can be administered with or without food.

The following formulation examples are illustrative only and are not intended to limit the scope of the inventions in any way.

EXAMPLES

Five versions of compound (1), namely the free acid, sodium, potassium, tromethamine and meglumine salts were produced and their physical properties and manufacturability potential guided the selection of an preferred form of the compound.

E) Example Synthesis

To obtain the compounds described in the examples below and their corresponding analytical data, the following experimental and analytical protocols were adhered to unless otherwise indicated. Unless otherwise stated, reaction mixtures were magnetically stirred at room temperature (rt), solutions were generally "dried" over a drying agent such as $Na_2SO_4$ or $MgSO_4$, and mixtures, solutions, and extracts were typically "concentrated" on a rotary evaporator under reduced pressure.

Data Analysis Setup

Thin-layer chromatography (TLC) was performed using Merck silica gel 60 $F_{254}$ 2.5 cm×7.5 cm 250 µm or 5.0 cm×10.0 cm 250 µm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with hexanes/ethyl acetate, unless otherwise noted, whereas reversed-phase HPLC was performed on a Hewlett Packard HPLC Series 1100, with a Phenomenex Luna $C_{18}$ (5 µm, 4.6×150 mm) column, and detection was done at λ=230, 254 and 280 nm with a gradient of 10 to 99% acetonitrile/water (0.05% trifluoroacetic acid) over 5.0 min with a flow rate of 1 mL/min.

Alternately, preparative HPLC purification was performed on a Gilson automated HPLC system running Gilson Unipoint LC software with UV peak detection done at λ=220 nm and fitted with a reverse phase YMC-Pack ODS-A (5 µm, 30×250 mm) column; mobile gradient of 10-99% of acetonitrile/water (0.05% trifluoroacetic acid) over 15-20 min and flow rates of 10-20 mL/min.

Mass spectra (MS) were obtained on an Agilent series 1100 MSD equipped with a ESI/APCI positive and negative multimode source unless otherwise indicated, and nuclear magnetic resonance (NMR) spectra were obtained on Bruker model DRX spectrometers with the $^1$H NMR data showing chemical shifts in ppm downfield of the tetramethylsilane reference (apparent multiplicity, coupling constant J in Hz, integration).

Example 1

Free acid of 1-(5,6-Dichloro-1H-benzoimidazol-2-yl)-1H-pyrazole-4-carboxylic acid (compound (1))

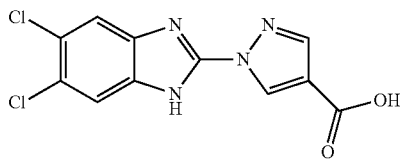 [SMILES: O=C(O)c1cnn(-c2nc3cc(Cl)c(Cl)cc3[nH]2)c1]

Method A:

The free acid of compound (1) was prepared by using 2,5,6-trichloro-1H-benzoimidazole and 1H-pyrazole-4-carboxylic acid. MS (ESI/CI): mass calculated for $C_{11}H_6Cl_2N_4O_2$, 297.1; m/z found, 296.0 [M−H]$^−$. $^1$H NMR (500 MHz, DMSO-d$_6$): 14.18-12.52 (br s, 2H), 8.89 (d, J=0.5 Hz, 1H), 8.31 (d, J=0.5 Hz, 1H), 7.80 (s, 2H).

Method B:

Step A: 5,6-Dichloro-1,3-dihydro-benzoimidazol-2-one: To the solution of 4,5-dichloro-benzene-1,2-diamine (25 g, 0.14 mol) in dry DMF (200 mL), was added CDI (23 g, 0.14 mol) as the solid. The reaction solution was stirred at room temperature for 1 hour, then water (500 mL) was added. The precipitated solid was collected by filtration, washed with water, dried thoroughly to afford the titled compound (26.0 g, 90%). The crude product was used in the following reaction without further purification.

Step B: 2,5,6-Trichloro-1H-benzoimidazole: Thoroughly dried 5,6-dichloro-1,3-dihydro-benzoimidazol-2-one (28.4 g, 0.14 mol) was suspended in POCl$_3$ (75 mL). The reaction solution was heated to reflux temperature for 3 hours and cooled to room temperature. The solution was poured into crushed ice/water (1.5 L) slowly with sufficient stirring. The solution was neutralized to pH=7.0 with NaOH. The precipitated solid was collected by filtration, washed with water, and dried to afford the title compound (27.9 g, 90%). The crude product was used in the following reaction without further purification.

Step C: 1-(5,6-Dichloro-1-dimethylsulfamoyl-1H-benzoimidazol-2-yl)-1H-pyrazole-4-carboxylic acid ethyl ester. 2,5,6-Trichloro-1H-benzoimidazole 2 (27.6 g, 0.125 mol) was dissolved in dry DMF (200 mL) and then K$_2$CO$_3$ (20.7 g, 0.15 mol) and dimethylsulfamoyl chloride (17.9 g, 0.125 mol) were added. The reaction mixture was stirred at room temperature for 16 hours. HPLC analysis showed the complete formation of 2,5,6-trichloro-benzoimidazole-1-sulfonic acid dimethylamide. In the same pot, without isolation of 2,5,6-trichloro-benzoimidazole-1-sulfonic acid dimethylamide, was added 1H-pyrazole-4-carboxylic acid ethyl ester (17.5 g, 0.125 mol) and K$_2$CO$_3$ (20.7 g, 0.15 mol). The reaction mixture was stirred at 70° C. for 4 hours and water (500 mL) was added while the reaction solution was still hot. The reaction solution was cooled to room temperature. The precipitated solid was collected via filtration, washed with water and dried. The crude product was used in the following reaction without further purification.

Step D: 1-(5,6-Dichloro-1H-benzoimidazol-2-yl)-1H-pyrazole-4-carboxylic acid. Crude 1-(5,6-Dichloro-1-dimethylsulfamoyl-1H-benzoimidazol-2-yl)-1H-pyrazole-4-carboxylic acid ethyl ester was dissolved in THF (125 mL) and LiOH.H$_2$O (21 g, 0.5 mol) in water (250 mL) was added. The reaction mixture was stirred at reflux temperature for 2 hours and cooled to room temperature. Concentrated HCl was added to adjust pH to 2.0. The solid precipitated was collected by filtration, washed with water and dried. The solid was triturated in hot EtOAc (1 L). After cooling to room temperature and filtration, the compound of Formula (I) was obtained as a tan solid (18.5 g, 50%). MS [M+H]$^+$ found 297.0. $^1$H NMR (500 MHz, DMSO-d$_6$): 13.71 (s, 1H), 12.99 (s, 1H), 8.90 (s, 1H), 8.32 (s, 1H), 7.94 (s, 1H), 7.67 (s, 1H).

The thermal properties, crystalline nature, apparent purity and moisture uptake of a 6.0 g batch of the free acid of compound (1) are summarized in Table 1. Saturation data for compound (1) is shown in FIG. 1.

TABLE 1

| Apparent Purity (HPLC) | Crystallinity (PXRD) | Melting Point (DSC) | Adsorption (40-90% RH) | Desorption (90-0% RH) |
|---|---|---|---|---|
| 99.8% | Weakly crystalline | 343° C.$^a$ | +0.59% | −0.96% |

$^a$decomposition

Example 2

Potassium Salt of Compound (1)

The potassium salt of 1-(5,6-dichloro-1H-benzoimidazol-2-yl)-1H-pyrazole-4-carboxylic acid was prepared by suspending the free acid (55 g, 1.7 mol) in EtOH (1.5 L) at reflux temperature with K$_2$CO$_3$ (12.79 g, 0.85 mol) in 20 mL water added dropwise over 5 min. Strong mechanic stirring was required to ensure proper agitation. The suspension was stirred at reflux temperature for eight hours and then cooled to room temperature over five hours. The precipitated solid was collected by filtration and quickly washed with 100 mL of water followed by EtOH. The potassium salt was obtained as a white solid (38 g, 65%). Subsequently, the mother liquor was concentrated and the above process was repeated once to give the second crop of the potassium salt (13 g, 22%). MS [M+H]$^+$=297.0. $^1$H NMR (500 MHz, DMSO-d$_6$): 8.65 (s, 1H), 7.96 (s, 1H), 7.57 (s, 2H).

The potassium salt as prepared by the above re-slurry methodology is non-hygroscopic and consistent with a poorly crystalline hydrate as seen by PXRD and thermal analysis. Two broad endothermic peaks of the potassium salt of compound (1) were seen by DSC that can be associated with a dehydration event and melt/decomposition, respectively (Table 2).

TABLE 2

| Apparent Purity (HPLC) | Crystallinity (PXRD) | Melting Point (DSC) | Adsorption (40-90% RH) | Desorption (90-0% RH) |
|---|---|---|---|---|
| 100.0% | crystalline monohydrate | 277° C.[d] | +0.53% | −0.89% |

[d]decomposition

Example 3

Sodium Salt of Compound (1)

The sodium salt of compound (1) is a poorly crystalline, hydrated solid as shown by PXRD and thermal analysis. The DSC reveals two broad endothermic peaks; the first event is associated with a loss of water (~9% by TGA), while the second endotherm is caused by melting/decomposition of the salt. The sodium salt was prepared in a method similar to that used to prepare the potassium salt (slurry method).

Example 4

Crystallization Procedure of the Tromethamine Salt of Compound (1)

Two forms of the tromethamine salt have been produced to date. The first form was obtained from the slurry of compound (1) and tromethamine in aqueous ethanol (14% water). Although not a salt, this physical mixture was not pursued. The second form was produced from an aqueous workup containing excess amounts of counterion. This form was a hydrated salt that was observed to have a lower apparent aqueous solubility than the potassium salt. This compound also exhibited poor bulk properties.

Example 5

Crystallization Procedure of the Meglumine Salt of Compound (1)

A clear solution (30 mg/mL) of the free acid of compound (1) and 1.2 molar equivalent of meglumine was produced in aqueous methanol (12% water) following slight heating. Room temperature stirring with seeding or refrigeration with or without seeding consistently led to crystallization of the meglumine salt, which was collected via filtration. This methodology was used to produce a 2 g batch of the salt. The solvent composition in the above procedure was modified to aqueous ethanol and used by the PDMS API SM Development team to produce 8.7-kg of GMP-grade material in support of FIH-enabling and FIH studies.

Figure 2:
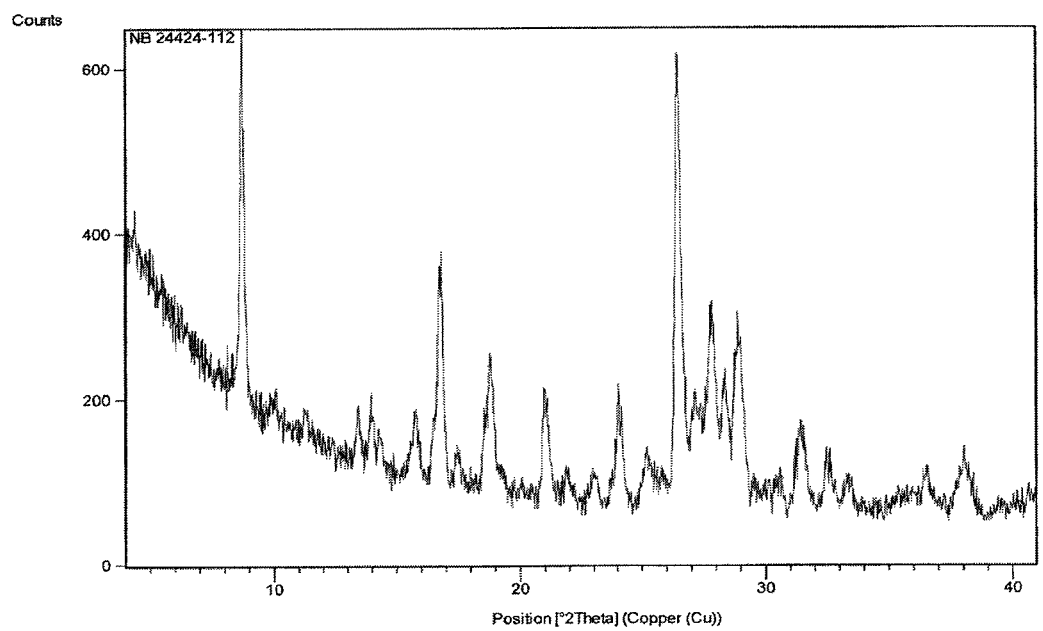
FIG. 2 shows PXRD data of the meglumine salt of compound (1).
Figure 3:
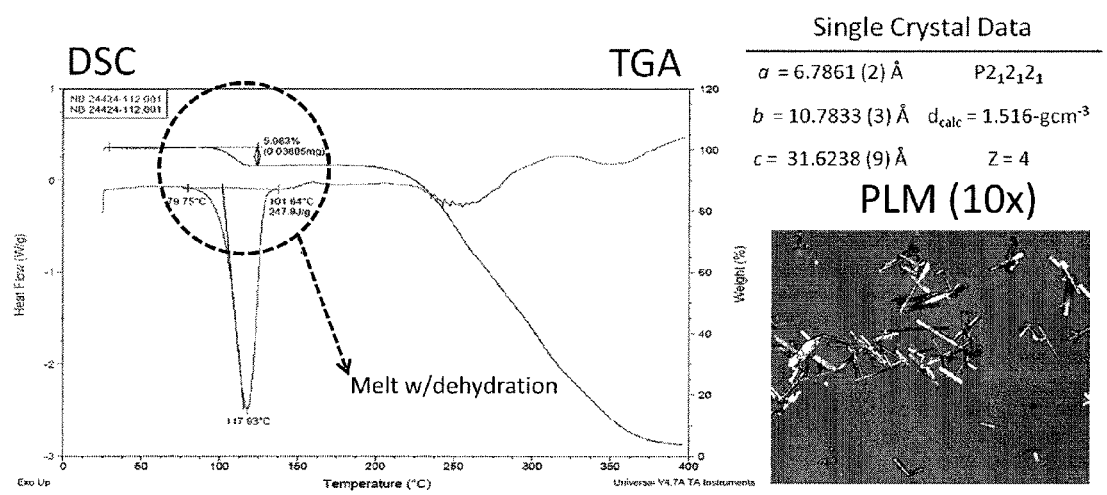
FIG. 3 shows DSC, TGA and x-ray data of the meglumine salt of compound (1).
Figure 4:
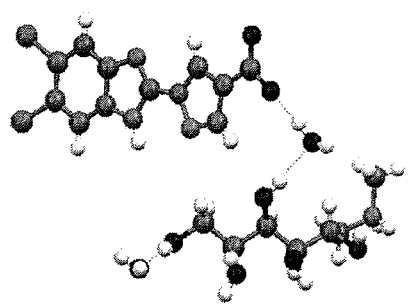
FIG. 4 shows: (A) the single crystal structure of the meglumine salt of compound (1); and (B) the experimental and stimulated powder pattern of a single crystal for the meglumine salt of compound (1).
Figure 4:
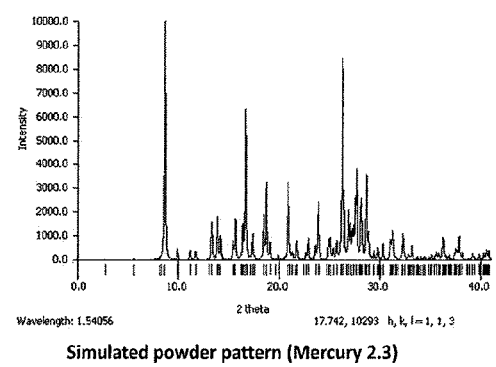

The thermal properties, crystalline nature, and apparent purity of the meglumine salt of compound (1) are summarized in Table 3. FIGS. 2 and 3 show salt bulk properties of the meglumine salt of compound (1), including PXRD data and DSC, TGA and x-ray data, respectively. The single crystal data confirmed the meglumine salt of compound (1) to be a dihydrate with the simulated powder pattern in excellent agreement with the experimental powder pattern as shown in FIGS. 4A and 4B. The meglumine salt of compound (1) was observed to have improved bulk properties, solubility, and enhanced processability compared to the free acid or the potassium salt of compound (1).

TABLE 3

| Sample ID | Apparent Purity (HPLC) | Crystallinity (PXRD) | Melting Point (DSC) |
|---|---|---|---|
| Meglumine salt of compound (1) | >99.9% | crystalline dihydrate | 80° C. |

Example 6

Topical Formulations of Meglumine Salt of Compound (1)

Materials and excipients that used in the development of topical formulations of a meglumine salt of compound (1) are listed in Table 4.

TABLE 4

| Materials |
|---|
| Meglumine salt of compound (1) |
| Hydroxypropyl Methylcellulose (HPMC K15M) |
| Poloxamer 407* |
| Methylcellulose (MC) |
| PEG4000 |
| Meglumine (NMDG) |
| Vitamin E-TPGS |
| Carbomer 941 |
| Carbomer 934P |
| Carboxymethylcellulose (Na-CMC) |
| HP-β-CD |
| Sterile Water for Irrigation |

*solubilization at 5° C. due to the thermo-reversible property of the excipient.

Table 5 lists the physical and chemical stability results performed on selected formulations of the meglumine salt of compound (1) after 4 weeks of storage.

TABLE 5

| Formulation | | Meglumine salt of compound (1) remaining (%) | | |
|---|---|---|---|---|
| Experiment | Composition | 2° C. | 20° C. | 40° C. |
| 1 | 0.5% HPMC K15M (pH 8.33) | 99.89 | 101.14 | 101.44 |
| 2 | 1.0% HPMC K15M (pH 8.33) | 99.59 | 99.21 | 99.08 |
| 3 | 2.0% Methylcellulose (pH 8.32) | 98.49 | 99.71 | 97.20 |
| 4 | 15% Poloxamer 407 (pH 8.10) | 99.19 | 100.03 | 87.29* |
| 5 | 20% Poloxamer 407 (pH 8.03) | 97.60 | 99.57 | 96.43* |
| 6 | VitE-TPGS/PEG4000/water (20:20:60; pH 8.06) | 100.27 | 100.32 | 98.87 |

*Precipitation observed in the vial

HPLC analysis showed that the six formulation compositions were chemically stable for four weeks under the studied storage conditions. The apparent loss of mass balance for the poloxamer-based formulation (Experiment 4) was attributed to the precipitation of the free acid of compound (1) at 40° Celsius and not degradation. At 40° Celsius, the polymers degraded that resulted in the formation of acetic acid, aldehydes, and a concurrent loss of viscosity and drop in pH. The resulting acidic environment caused precipitation of the insoluble free acid of compound (1) and discoloration of the formulation. The instability of poloxamer (or lutrol) is known and has been disclosed in Erlandsson, B., 2002, *Polym. Degrad. and Stab.*, 78:571-575. Such a degradation was not observed in samples stored at room temperature or refrigerated.

The results of the solubility screen of formulations of the meglumine salt of compound (1) are shown in Table 6. Four of the ten vehicles investigated, namely 1% Na-CMC (Experiment 1), 1% Carbomer 941 (Experiment 2), 1% Carbomer 934P (Experiment 3) and 20% HP-β-CD (Experiment 4), did not meet the targeted solubility criterion of 10 mg/mL (free acid equivalent) or were toxic to Hela cells. The 1% MC vehicle did not have notable advantages over the product containing 2% MC. The meglumine salt of compound (1) was sufficiently soluble within an acceptable pH range (6-8.5) in Experiments 5 and 7-11.

TABLE 6

| Experiment | Formulation Composition | Compound (1) Solubility |
|---|---|---|
| 1 | 1% Na-CMC | <10 mg/mL |
| 2 | 1% Carbomer 941 | <10 mg/mL |
| 3 | 1% Carbomer 934P | <10 mg/mL |
| 4 | 0.5% HPMC K15M | ≥10 mg/mL |
| 5 | 1.0% HPMC K15M | ≥10 mg/mL |
| 6 | 1% Methylcellulose | ≥10 mg/mL |
| 7 | 2% Methylcellulose | ≥10 mg/mL |
| 8 | 15% Poloxamer 407 | ≥10 mg/mL |
| 9 | 20% Poloxamer 407 | ≥10 mg/mL |
| 10 | VitE-TPGS/PEG4000/water (20:20:60) | ≥10 mg/mL |
| 11 | 20% HP-β-CD* | ≥10 mg/mL |

*Formulation was toxic to the Hela cells

F) Biological Examples

Cellular Assay for HIF1-α

Figure 5:
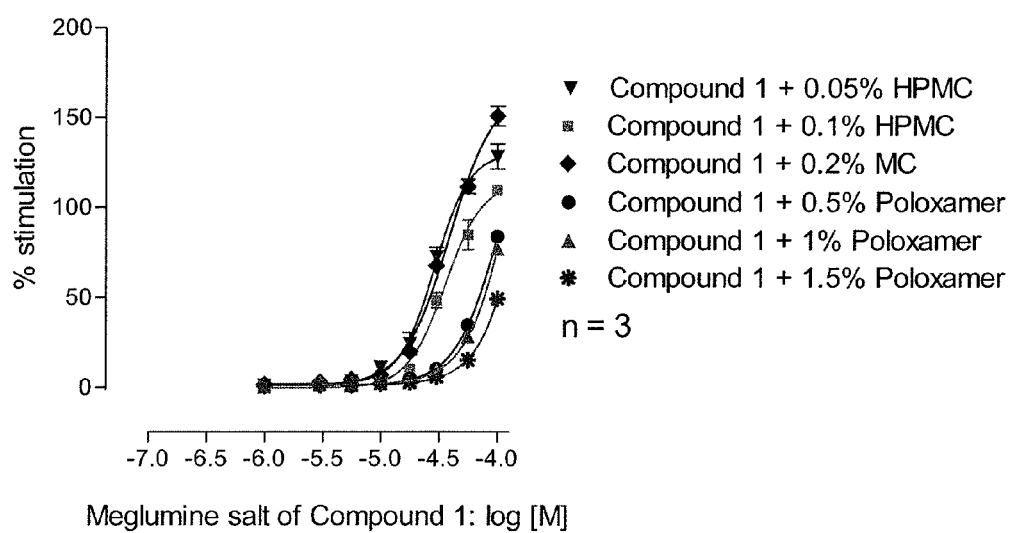
FIG. 5 shows the percentage stimulation of HIF1-α upon exposure of formulations of the meglumine salt of compound (1).

Hela cells (ATCC, Manassas, Va.) were plated in 96-well plates at 20,000 cells per well in 100 μl of DMEM containing 10% fetal bovine serum, 1% non-essential amino acids, 50 IU/mL of penicillin and 50 μg/mL of streptomycin (all cell culture reagents from Invitrogen, Carlsbad, Calif.). 24 hours after plating, changed media to 100 μl of DMEM without 10% fetal bovine serum, 1.1 μl of the stock solution for each compound was added and incubated for six hours. All compounds were tested with a final compound concentration of 100 μM. The supernatant was removed and the cells were lysed in 55 μl of MSD lysis buffer containing protease inhibitors. 50 μl of the cell lysate was then transferred to a blocked MSD human HIF-1α detection plate (Meso-Scale Discovery, Gaithersburg, Md., as per manufacturers protocol), and incubated at room temperature on an orbital shaker for two hour. After three washes in PBS, 25 μl of 20 nM anti-HIF1α detection antibody was added and incubated for 1 hour at room temperature on an orbital shaker. After three washes in PBS, 150 μl of 1× read buffer was added and the plate was then read on a MSD SECTOR instrument. Data was analyzed by determining the percent of HIF stimulation in the presence of 100 μM compound relative to an assay control compound, 7-[(4-Chloro-phenyl)-(5-methyl-isoxazol-3-ylamino)-methyl]-quinolin-8-ol. This biological data for the meglumine salt of compound (1) is presented in FIG. 5.

Figure 6:
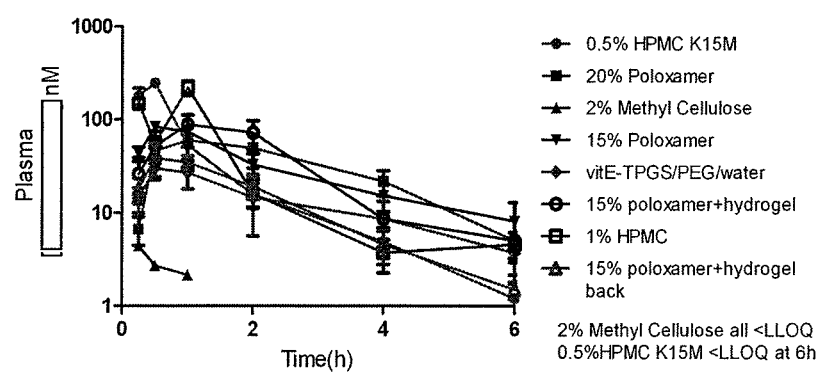
FIG. 6 shows plasma levels (systemic burden) in wounded mice after topical application of formulations of the meglumine salt of compound (1).
Figure 7:
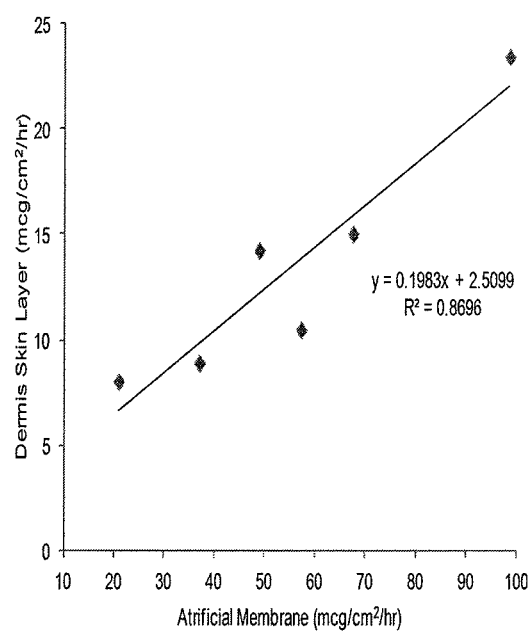
FIG. 7 shows the correlation of the flux of compound (1) across skin (human dermis) and an artificial membrane using a Franz diffusion cell upon application of a formulation of meglumine salt of compound (1).
Figure 8:
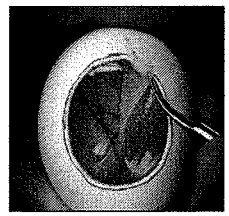
FIG. 8 shows no to very low irritation caused by application of a formulation of the meglumine salt of compound (1) as tested in a HET-CAM assay.
Figure 8:
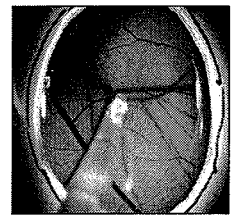

Additional biological data for formulations of the meglumine salt of compound (1) is presented in FIGS. 6 through 8.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of formula

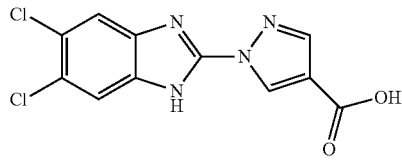

in the form of the dihydrate meglumine salt.

2. A pharmaceutical composition comprising the dihydrate meglumine salt of the compound of formula given in claim 1 and a pharmaceutically acceptable excipient.

3. A topical ointment comprising the pharmaceutical composition of claim 2.

* * * * *